(12) United States Patent
Verkman et al.

(10) Patent No.: US 9,316,633 B2
(45) Date of Patent: *Apr. 19, 2016

(54) METHODS FOR IDENTIFYING INHIBITORS OF SOLUTE TRANSPORTERS

(75) Inventors: Alan S. Verkman, San Francisco, CA (US); Marc Harris Levin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1370 days.

This patent is subject to a terminal disclaimer.

(21) Appl. No.: 12/514,992

(22) PCT Filed: Nov. 16, 2007

(86) PCT No.: PCT/US2007/085017
§ 371 (c)(1),
(2), (4) Date: Mar. 18, 2010

(87) PCT Pub. No.: WO2008/067196
PCT Pub. Date: Jun. 5, 2008

(65) Prior Publication Data
US 2010/0190796 A1    Jul. 29, 2010

Related U.S. Application Data

(60) Provisional application No. 60/859,665, filed on Nov. 16, 2006, provisional application No. 60/859,666, filed on Nov. 16, 2006, provisional application No. 60/859,800, filed on Nov. 16, 2006.

(51) Int. Cl.
| | |
|---|---|
| G01N 33/50 | (2006.01) |
| G01N 33/62 | (2006.01) |
| G01N 33/68 | (2006.01) |
| G01N 33/80 | (2006.01) |

(52) U.S. Cl.
CPC ............ *G01N 33/5026* (2013.01); *G01N 33/62* (2013.01); *G01N 33/6872* (2013.01); *G01N 33/80* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 5,302,608 | A * | 4/1994 | Sohda et al. ................... | 514/371 |
| 5,751,629 | A | 5/1998 | Nova et al. ..................... | 365/151 |
| 5,789,172 | A | 8/1998 | Still et al. ........................... | 435/6 |
| 5,798,035 | A | 8/1998 | Kirk et al. ..................... | 205/335 |
| 6,284,113 | B1 | 9/2001 | Bjornson et al. .............. | 204/453 |
| 6,454,924 | B2 | 9/2002 | Jedrzejewski et al. ......... | 204/601 |
| 6,681,788 | B2 | 1/2004 | Parce et al. ..................... | 137/14 |
| 6,878,755 | B2 | 4/2005 | Singh et al. ................... | 522/100 |
| 6,969,850 | B2 | 11/2005 | Staats ........................... | 250/288 |
| 8,394,788 | B2 * | 3/2013 | Verkman et al. ......... | 514/217.08 |
| 2010/0305105 | A1 | 12/2010 | Verkman et al. ......... | 514/217.08 |

FOREIGN PATENT DOCUMENTS

| | | |
|---|---|---|
| EP | 0 774 464 | 5/1997 |
| WO | WO 92/00091 | 1/1992 |
| WO | WO 92/07264 | 4/1992 |
| WO | WO 92/09300 | 6/1992 |
| WO | WO 95/16918 | 6/1995 |
| WO | WO 2004/077010 | 9/2004 |
| WO | WO 2008/061247 | 5/2008 |
| WO | WO 2008/061248 | 5/2008 |
| WO | WO 2008/067196 | 6/2008 |

OTHER PUBLICATIONS

Fenton et al. "Increased collecting duct urea transporter expression in Dahl salt-sensitive rats". American Journal of Physiology. Jul. 2003, vol. 285, No. 1, part. 2, pp. F143-F151.*
Wang et al. "Decreased abundance of collecting duct urea transporters UT-A1 and UTA3 with ECF volume expansion". American Journal of Physiology. Jul. 2003, vol. 282, No. 4, part. 2, pp. F577-F584.*
Peerce et al. "Effect of 2-phosphophloretin on renal function in chronic renal failure rats". Am J Physiol Renal Physiol, 2004, 287 (1), pp. F48-F56.*
Steward et al. Am J Physiol Regul Integr Comp Physiol, 2005, 289: pp. R605-R612.*
Bagnasco et al., "Cloning and characterization of the human urea transporter UT-A1 and mapping of the human Slc14a2 gene," *American Journal of Physiology & Renal Physiology*, 281:F400-F406, 2001.
Bagnasco, S. M., "Gene structure of urea transporters," *American Journal of Physiology & Renal Physiology*, 284:F3-F10, 2003.
Bagnasco, S. M., "Role and regulation of urea transporters," *Pflügers Archive: European Journal of Physiology*, 450(4):217-226, 2005.
Cohn et al., "Extracellular lysines on the plasmodial surface anion channel involved in Na+ exclusion," *Molecular & Biochemical Parasitology*, 132:27-34, 2003.
Fröhlich et al., "Urea transport in MDCK cells that are stably transfected with UT-A1," *American Journal of Physiology & Cell Physiology*, 286:C1264-C1270, 2004.
Fröhlich et al., "Regulation of UT-A1-mediated transepithelial urea flux in MDCK cells," *American Journal of Physiology & Cell Physiology*, 291:C600-C606, 2006.
Gnudi et al., "The link between Glut-1 and hypertension in diabetic nephropathy," *Current Hypertension Reports*, 8:79-83, 2006.
Goldsmith, S. R., "Current Treatments and Novel Pharmacologic Treatments for Hyponatremia in Congestive Heart Failure," *The American Journal of Cardiology*, 95(9A):14B-23B, 2005.

(Continued)

*Primary Examiner* — Vera Afremova
(74) *Attorney, Agent, or Firm* — Seed IP Law Group PLLC

(57) ABSTRACT

Provided herein are methods for identifying and characterizing agents that alter the volume of a cell. Methods are provided for rapid screening and identification of an agent that alters the capability of a small, neutrally charged solute transporter to transport the solute across a cell membrane. The methods described herein may be used to identify and characterize inhibitors of urea transporters, to identify and characterize inhibitors of aquaporins, and to identify and characterize inhibitors of other small, neutrally charged solutes such as glucose.

3 Claims, 7 Drawing Sheets

(56) References Cited

OTHER PUBLICATIONS

Goodman, B. E., "Transport of small molecules across cell membranes: water channels and urea transporters," *Advances in Physiology Education*, 26(3):146-157, 2002.
Guo et al., "Glucose Transporter 1, Distribution in the Brain and in Neural Disorders: Its Relationshop With Transport of Neuroactive Drugs Through the Blood-Brain Barrier," *Biochemical Genetics*, 43(3/4):175-187, 2002.
Hansen et al., "Aquaporin expression and cell volume regulation in the SV40 immortalized rat submandibular acinar cell line," *Pflügers Archive: European Journal of Physiology*, 453(6):787-796, 2007.
Ishibashi et al., "The Dichotomy of MIP Family Suggests Two Separate Origins of Water Channels," *News in Physiological Sciences*, 13:137-142, 1998.
Karakashian et al., "Cloning and Characterization of Two New Isoforms of the Rat Kidney Urea Transporter: UT-A3 and UT-A4," *Journal of the American Society of Nephrology*, 10:230-237, 1999.
Klein et al., "Upregulation of Urea Transporter UT-A2 and Water Channels AQP2 and AQP3 in Mice Lacking Urea Transporter UT-B," *Journal of the American Society of Nephrology*, 15:1161-1167, 2004.
Leroy et al., "Hyperosmotic NaCI and Urea Synergistically Regulate the Expression of the UT-A2 Urea Transporter in Vitro and in Vivo," *Biochemical and Biophysical Research Communications*, 271(2):368-373, 2000.
Leturque et al., "The role of GLUT2 in dietary sugar handing," *Journal of Physiology and Biochemistry*, 61(4):529-537, 2005.
Levin et al., "Urearetics: a small molecule screen yields nanomolar potency inhibitors of urea transporter UT-B," *The FASEB Journal*, 21:551-536, 2007.
Lucien et al., "Characterization of the Gene Encoding the Human Kidd Blood Group/Urea Transporter Protein," *The Journal of Biological Chemistry*, 273(21):12973-12980, 1998.
Ma et al., "Severely Impaired Urinary Concentrating Ability in Transgenic Mice Lacking Aquaporin-1 Water Channels," *The Journal of Biological Chemistry*, 273(8):4296-4299, 1998.
Macey et al., "Independence of Water and Solute Pathways in Human RBCs," *Journal of Membrane Biology*, 134(3):241-250, 1993.
Magni et al., "Proteomic knowledge of human aquaporins," *Proteomics*, 6:5637-5649, 2006.
Manolescu et al., "Identification of a Hydrophobic Residue as a Key Determinant of Fructose Transport by the Facilitative Hexose Transporter SLC2A7 (GLUT7)," *The Journal of Biological Chemistry*, 280(52):42978-42983, 2005.
Martial et al., "Urea derivatives as tools for studying the urea-facilitated transport system," *Pflügers Archive: European Journal of Physiology*, 423:51-58, 1993.
Maurer et al., "Adult neural stem cells express glucose transporters GLUT1 and GLUT3 and regulate GLUT3 expression," *FEBS Letters*, 580:4430-4434, 2006.
Mayrand et al., "Urea and Ethylene Glycol-facilitated Transport Systems in the Human Red Cell Membrane," *The Journal of General Physiology*, 81:221-237, 1983.
Mazeron et al., "A Theoretical Approach of the Measurement of Osmotic Fragility of Erythrocytes by Optical Transmission," *Photochemistry and Photobiology*, 72(2):172-178, 2000.
McGee et al., "Exercise and skeletal muscle glucose transporter 4 expression: molecular mechanisms," *Clinical and Experimental Pharmacology & Physiology*, 33:395-399, 2006.

Miller, M., "Hyponatremia and Arginine Vasopressin Dysregulation: Mechanisms, Clinical Consequences, and Management," *Journal of the American Geriatrics Society*, 54(2):345-353, 2006.
Moehlenbrock et al., "Use of microchip-based hydrodynamic focusing to measure the deformation-induced release of ATP from erythrocytes," *The Analyst*, 131:930-937, 2006.
Patelaros, S. V., "Influence of divalent cations $Ca^{2+}$ and $Zn^{2+}$ on the activation of posthypertonic hemolysis of human erythrocytes," XP002477836 Database accession No. PREV199900540544, abstract.
Patelaros, S. V., "Influence of divalent cations $Ca^{2+}$ and $Zn^{2+}$ on the activation of posthypertonic hemolysis of human erythrocytes," *Biopolimery I Kletka*, 15(1):43-48, 1999.
Sands et al., "Urea transporters in kidney and erythrocytes," *The American Journal of Physiology*, 273:F321-F339, 1997.
Sands et al., "Regulation of Urea Transporter Proteins in Kidney and Liver," *The Mount Sinai Journal of Medicine*, 67(2):112-119, 2000.
Sands, J. M., "Mammalian Urea Transporters," *Annual Review of Physiology*, 65:543-566, 2003.
Sands, J. M., "Renal urea transporters," *Current Opinion in Nephrology and Hypertension*, 13(5):525-532, 2004.
Shayakul et al., "The SLC14 gene family of urea transporters," *Pflügers Archive: European Journal of Physiology*, 447:603-609, 2004.
Sidoux-Walter et al., "At Physiological Expression Levels the Kidd Blood Group/Urea Transporter Protein Is Not a Water Channel," *The Journal of Biological Chemistry*, 274(42):30228-30235, 1999.
Tamarappoo et al., "High-Throughput Screening of Combinatorial Drug Libraries to Identify Non-Mercurial Aquaporin Inhibitors," *Journal of the American Society of Nephrology*, 10: 25A, 1999, XP000861840, ISSN: 1046-6673 abstract.
Thorsen et al., "Microfluidic Large-Scale Integration," *Science*, 298:580-584, 2002.
Tradtrantip et al., "Aquaporin water channels in transepithelial fluid transport," *The Journal of Medical Investigation*, 56:179-184, 2009.
Tsukaguchi et al., "Cloning and Characterization of the Urea Transporter UT3," *The Journal of Clinical Investigation*, 99(7):1506-1515, 1997.
Verkman, A. S., "Physiological importance of aquaporins: lessons from knockout mice," *Current Opinion in Nephrology and Hypertension*, 9(5):517-522, 2000.
Verkman, A. S., "Roles of Aquaporins in Kidney revealed by Transgenic Mice," *Seminars in Nephrology*, 26:200-208, 2006.
Yang et al., "Urea Transporter UT3 Functions as an Efficient Water Channel," *The Journal of Biological Chemistry*, 273(16):9369-9372, 1998.
Yang et al., "Urea-selective Concentrating Defect in Transgenic Mice Lacking Urea Transporter UT-B," *The Journal of Biological Chemistry*, 277(12):10633-10637, 2002.
Yang et al., "Analysis of Double Knockout Mice lacking Aquaporin-1 and Urea Transporter UT-B," *The Journal of Biological Chemistry*, 277(39):36782-36786, 2002.
"Thiourea: CAS No. 62-56-6," *Report on Carcinogens, Twelfth Edition*, National Toxicology Program, Department of Health and Human Services, pp. 407-408, 2011.
Fischer Scientific, "Material Safety Data Sheet: Thiourea," ACC# 23420, created Jun. 4, 1999, revised Jun. 26, 2006, 8 pages.

\* cited by examiner

METHODS FOR IDENTIFYING INHIBITORS OF SOLUTE TRANSPORTERS

CROSS-REFERENCE TO RELATED APPLICATIONS

This application is a U.S. national stage application filed under 35 U.S.C.§371 of International Patent Application PCT/US2007/085017, accorded an international filing date of Nov. 16, 2007, which claims the benefit of U.S. Provisional Application No. 60/859,665 filed Nov. 16, 2006, U.S. Provisional Application No. 60/859,666 filed Nov. 16, 2006, and U.S. Provisional Application No. 60/859,800 filed Nov. 16, 2006, all of which are incorporated herein by reference in their entirety.

STATEMENT OF GOVERNMENT INTEREST

This invention was made with government support under Grant No. DK35124 awarded by National Institutes of Health. The government has certain rights in this invention.

BACKGROUND OF THE INVENTION

1. Field of the Invention

Agents that alter the transport activity of small, neutrally charged solutes by solute transporters and agents that alter transport of water by aquaporins are needed as therapeutic agents for increasing solute clearance in states of fluid overload and for treating diseases, disorders, and conditions such as hypertension. Methods for identifying and using agents that inhibit solute transporters and aquaporins are described herein.

2. Description of the Related Art

Diuretics are administered widely in humans to increase renal salt and water clearance in a variety of conditions that are associated with total body fluid overload, such as congestive heart failure and cirrhosis, as well in normovolemic states such as hypertension and syndrome of inappropriate secretion of antidiuretic hormone (SIADH). Most diuretics are inhibitors of salt absorption by kidney tubules, such as a furosemide block of $Na^+/K^+/2Cl^-$ co-transport in the thick ascending limb of Henle and a thiazide block of $Na^+/Cl^-$ co-transport in the distal tubule. Recently, a new type of diuretic, called an "aquaretic," has been developed to increase renal water clearance in hyponatremia associated with fluid overload or SIADH (see, e.g., Goldsmith, *Am. J. Cardiol.* 95:14 B-23B (2005); Miller, *J. Am. Geriatr. Soc.* 54:345-53 (2006)). Vasopressin-2 receptor (V2R) antagonist aquaretics have been approved for clinical use in some countries, though not yet in the United States, and aquaporin inhibitor aquaretics are under development.

Functional studies in knock-out mice indicate a critical role for solute transporters, such as urea transporters (UTs), in the urinary concentrating mechanism and in renal urea clearance. However, potent and specific urea transport blockers have not been available. Accordingly, a third type of diuretic is needed: one that targets renal urea clearance mechanisms. Because urea is of at least equal importance to NaCl in the renal countercurrent mechanism for urinary concentration (see, e.g., Bankir et al., supra; Masilamani et al., *In The Kidney* (6th Edition), Brenner, ed. Philadelphia, Pa.; WB Saunders Company; pages 595-35; (2000)), such diuretics are needed for increasing solute clearance in states of fluid overload, for treating hypertension, and may also be useful in prolonging dialysis-free survival in chronic renal insufficiency. Therapeutic molecules are needed that are capable of effectively increasing renal water and solute clearance in subjects who are exhibiting a water-retaining state.

Thus, a need exists for methods that permit rapid screening and characterization of large numbers of agents to identify agents that alter the transport activity of solute transporters, such as agents that alter the transport activity of urea transporters. Methods are also needed in the art for rapid screening and identification of agents that alter the transport activity of aquaporins.

BRIEF SUMMARY OF THE INVENTION

In one embodiment, a method of identifying an agent that alters the volume of a cell is provided, which method comprises (a) preparing a first indicator cell sample and a second indicator cell sample, wherein each of the first and second indicator cell samples comprises one or a plurality of indicator cells combined with a first solution that comprises a neutrally charged solute in an amount sufficient to provide a hyperosmolar solution, wherein the indicator cells are derived from a biological sample (b) contacting a candidate agent with the first indicator cell sample, under conditions and for a time sufficient for the candidate agent to interact with the indicator cell; (c) subsequent to step (b), replacing the first solution from the first and second indicator cell samples with a second solution that lacks the neutrally charged solute to provide each of the first and second indicator cell samples in a substantially isosmolar solution; and (d) subsequent to step (c), comparing a first level of indicator cell lysis in the first indicator cell sample to a second level of indicator cell lysis in the second indicator cell sample, wherein a difference between the first and second levels indicates that the agent alters cell volume. In a certain embodiment, the agent that alters cell volume is capable of altering transport of the solute by a transporter polypeptide across a cell membrane of the indicator cell. In a particular embodiment, the transporter polypeptide is endogenously expressed by the indicator cell. Alternatively, the indicator cell comprises an exogenous polynucleotide that encodes the transporter polypeptide and that directs expression of the transporter polypeptide in the indicator cell.

In one specific embodiment, the indicator cell is a red blood cell, wherein the biological sample comprises red blood cells, and wherein the red blood cell is a red blood cell of a mammal, which is, for example, a human, a non-human primate, a mouse, a rat, a dog, or a cat. In a particular embodiment, the biological sample is whole blood. In a particular embodiment, altering transport of the solute across the cell membrane of the indicator cell comprises inhibiting transport of the solute by the transporter polypeptide across the cell membrane. In a specific embodiment, the transporter polypeptide is a urea transporter, wherein the urea transporter is a UT-B transporter. In another embodiment, the urea transporter is at least one UT-A transporter selected from a UT-A1 isoform, UT-A2 isoform, UT-A3 isoform, UT-A4 isoform, and UT-A5 isoform. In one embodiment, the first level of indicator cell lysis is greater than the second level of indicator cell lysis, thereby indicating that the agent is capable of altering transport of the solute by the urea transporter. In a specific embodiment, the first level of indicator cell lysis indicates lysis of 41% to 100% of the indicator cells in the first indicator cell sample and wherein the second level of indicator cell lysis indicates lysis of 0% to 40% of the indicator cells in the second indicator cell sample. In particular embodiments, the solute is selected from urea, a urea analogue, glycerol, a monosaccharide, and a disaccharide, wherein the urea analogue is selected from formamide, acetamide, propionamide, N-methylurea, butyramide, and isobutyramide. In one embodiment, when the solute is a urea analogue, the hyperosmolar solution comprises the urea analogue at a concentration of 1.0-1.5 M. In a particular embodiment, the indicator cell is a mouse red blood cell and the solute is N-methylurea, and in another particular embodiment, the indicator cell is a human red blood cell and the solute is acetamide. In a specific embodiment, the solute is urea and the hyperosmolar solution comprises 2.0-3.0 M urea, and the first level of indicator cell lysis indicates lysis of 41% to 100% of the indicator cells in the first indicator cell sample and the second level of indicator cell lysis indicates lysis of 0% to 40% of the indicator cells in the second indicator cell sample.

In another embodiment of the method of identifying an agent that alters the volume of a cell, the agent that alters cell volume is capable of altering transport of water by a transporter polypeptide across a cell membrane of the indicator cell. In a particular embodiment, altering transport of water across a cell membrane comprises inhibiting transport of water across the cell membrane, wherein inhibiting water transport across a cell membrane comprises inhibiting water transport by at least one aquaporin polypeptide. In specific embodiments, the at least one aquaporin (AQP) polypeptide is selected from AQP1, AQP2, AQP3, and AQP4. According to this embodiment, the first level of indicator cell lysis is less than the second level of indicator cell lysis, thereby indicating that the agent is capable of inhibiting water transport by the at least one aquaporin polypeptide. The solute is selected from urea, a urea analogue, a monosaccharide, and a disaccharide. In a particular embodiment, urea is the solute and the hyperosmolar solution comprises 2.5-5.0 M urea, and the first level of indicator cell lysis indicates lysis of 0% to 41% of the indicator cells in the first indicator cell sample, and the second level of indicator cell lysis indicates lysis of 41% to 100% of the indicator cells in the second indicator cell sample. In another specific embodiment, a urea analogue is the solute and the hyperosmolar solution comprises the urea analogue at a concentration of 2.0-3.5 M. In a particular embodiment, the solute is glucose and the hyperosmolar solution comprises glucose at a concentration of 2.0-3.5 M. In this embodiment of the method, wherein an agent alters the volume of the cell and the agent is capable of altering transport of water across a cell membrane, the first level of lysis determined indicates lysis of 0% to 41% of the indicator cells and the second level of lysis determined indicates lysis of 41% to 100% of the indicator cells.

According to particular embodiments of the methods described herein, the candidate agent is a member of a combinatorial library. In a specific embodiment, the candidate agent is a small molecule.

In another embodiment, provided herein is a method of identifying an agent that inhibits transport of urea across a cell membrane of a cell, which method comprises (a) preparing a first indicator cell sample and a second indicator cell sample, wherein each of the first and second indicator cell samples comprises one or a plurality of indicator cells combined with a first solution that comprises urea or an analogue thereof in an amount sufficient to provide a hyperosmolar solution, wherein the indicator cells are derived from a biological sample and wherein each indicator cell comprises at least one urea transporter polypeptide; (b) contacting a candidate agent with the first indicator cell sample, under conditions and for a time sufficient for the candidate agent to interact with the at least one urea transporter polypeptide of the indicator cell; (c) subsequent to step (b), replacing the first solution from the first and second indicator cell samples with a second solution that lacks urea to provide each of the first and second indicator cell samples in a substantially isosmolar solution; and (d) subsequent to step (c), comparing a first level of indicator cell lysis in the first indicator cell sample with a second level of indicator cell lysis in the second indicator cell sample, wherein the agent inhibits urea transport across a cell membrane if the first level of indicator cell lysis is greater than the second level of indicator cell lysis. In certain embodiments, the at least one urea transporter polypeptide is endogenously expressed by the indicator cell, and in other certain embodiments, the indicator cell comprises an exogenous polynucleotide that encodes the at least one urea transporter polypeptide and that directs expression of the at least one urea transporter polypeptide in the indicator cell. In one particular embodiment, the at least one urea transporter is a UT-B transporter. In other particular embodiments, the at least one urea transporter is at least one UT-A transporter selected from a UT-A1 isoform, UT-A2 isoform, UT-A3 isoform, UT-A4 isoform, and UT-A5 isoform. In other specific embodiments, the indicator cell is a red blood cell, and the biological sample comprises red blood cells, wherein the red blood cell is a red blood cell of a mammal. In particular embodiments, the mammal is a human, a non-human primate, a mouse, a rat, a dog, or a cat. In certain embodiments, the biological sample is whole blood. In certain embodiments of the method, the candidate agent is a member of a combinatorial library. In certain particular embodiments, the candidate agent is a small molecule. According to one embodiment of the method, the solute is selected from urea, a urea analogue, glycerol, a monosaccharide, and a disaccharide, wherein the urea analogue is selected from formamide, acetamide, propionamide, N-methylurea, butyramide, and isobutyramide. In a particular embodiment, the solute is a urea analogue and the hyperosmolar solution comprises the urea analogue at a concentration of 1.0-1.5 M. In a certain embodiment, the indicator cell is a mouse red blood cell and the solute is N-methylurea, and in another certain embodiment, the indicator cell is a human red blood cell and the solute is acetamide. In one embodiment, the first level of indicator cell lysis indicates lysis of 41% to 100% of the indicator cells in the first indicator cell sample and the second level of indicator cell lysis indicates lysis of 0% to 40% of the indicator cells in the second indicator cell sample. In a more specific embodiment, the solute is urea and the hyperosmolar solution comprises 2.0-3.0 M urea, wherein the first level of indicator cell lysis indicates lysis of 41% to 100% of the indicator cells in the first indicator cell sample and wherein the second level of indicator cell lysis indicates lysis of 0% to 40% of the indicator cells in the second indicator cell sample.

In another embodiment, provided herein is a method of identifying an agent that inhibits transport of water across a cell membrane, which method comprises (a) preparing a first indicator cell sample and a second indicator cell sample, wherein each of the first and second indicator cell samples comprises one or a plurality of indicator cells combined with a first solution that comprises a neutrally charged solute in an amount sufficient to provide a hyperosmolar solution, wherein the indicator cells are derived from a biological sample and wherein each indicator cell comprises at least one aquaporin polypeptide; (b) contacting a candidate agent with the first indicator cell suspension, under conditions and for a time sufficient for the candidate agent to interact with the at least one aquaporin polypeptide of the indicator cell; (c) subsequent to step (b), replacing the first solution from the first and second indicator cell samples with a second solution that lacks the neutrally charged solute to provide each of the first and second indicator cell samples in a substantially isosmolar solution; and (d) subsequent to step (c), comparing a first level of indicator cell lysis in the first indicator cell sample with a second level of indicator cell lysis in the second indicator cell sample, wherein the agent inhibits water transport across a cell membrane if the first level of indicator cell lysis is less than the second level of indicator cell lysis. In a specific embodiment, the at least one aquaporin polypeptide is endogenously expressed by the indicator cell, and in another specific embodiment, the indicator cell comprises an exogenous polynucleotide that encodes the at least aquaporin polypeptide and that directs expression of the at least one aquaporin polypeptide in the indicator cell. In certain specific embodiment, the at least one aquaporin (AQP) polypeptide is selected from AQP1, AQP2, AQP3, and AQP4. In other specific embodiments, the indicator cell is a red blood cell, and the biological sample comprises red blood cells, wherein the red blood cell is a red blood cell of a mammal. In particular embodiments, the mammal is a human, a non-human primate, a mouse, a rat, a dog, or a cat. In certain embodiments, the biological sample is whole blood. In certain embodiments of the method, the candidate agent is a member of a combinatorial library. In certain particular embodiments, the candidate agent is a small molecule. According to one embodiment of the method, the solute is selected from urea, a urea analogue, glycerol, a monosaccharide, and a disaccharide, wherein the urea analogue is selected from formamide, acetamide, propionamide, N-methylurea, butyramide, and isobutyramide. In a particular embodiment, urea is the solute and wherein the hyperosmolar solution comprises 2.5-5.0 M urea, wherein the first level of indicator cell lysis indicates lysis of 0% to 41% of the indicator cells in the first indicator cell sample, and wherein the second level of indicator cell lysis indicates lysis of 41% to 100% of the indicator cells in the second indicator cell sample. In another particular embodiment, a urea analogue is the solute and wherein the hyperosmolar solution comprises the urea analogue at a concentration of 2.0-3.5 M. In still another embodiment, the solute is glucose and wherein the hyperosmolar solution comprises glucose at a concentration of 2.0-3.5 M. According to these embodiments, the first level of indicator cell lysis indicates lysis of 0% to 41% of the indicator cells in the first indicator cell sample, and wherein the second level of indicator cell lysis indicates lysis of 41% to 100% of the indicator cells in the second indicator cell sample.

In still another embodiment, a method of identifying an agent that inhibits transport of a neutrally charged solute across a cell membrane of a cell is provided, which method comprises (a) preparing a first indicator cell sample and a second indicator cell sample, wherein each of the first and second indicator cell samples comprises one or a plurality of indicator cells combined with a first solution that comprises a neutrally charged solute in an amount sufficient to provide a hyperosmolar solution, wherein the indicator cells are derived from a biological sample and wherein each indicator cell comprises at least one transporter polypeptide that is capable of transporting the solute across a cell membrane; (b) contacting a candidate agent with the first indicator cell sample, under conditions and for a time sufficient for the candidate agent to interact with the at least one transporter polypeptide of the indicator cell; (c) subsequent to step (b), replacing the first solution from the first and second indicator cell samples with a second solution that lacks the neutrally charged solute to provide each of the first and second indicator cell samples in a substantially isosmolar solution; and (d) subsequent to step (c), comparing a first level of indicator cell lysis in the first indicator cell sample with a second level of indicator cell lysis in the second indicator cell sample, wherein the agent inhibits transport of the solute across a cell membrane if the first level of indicator cell lysis is greater than the second level of indicator cell lysis. In a particular embodiment, the solute is urea or an analogue thereof and the transporter polypeptide is a urea transporter polypeptide, wherein the analogue of urea is selected from formamide, acetamide, propionamide, N-methylurea, butyramide, and isobutyramide. In one specific embodiment, the at least one urea transporter is a UT-B transporter, and in another specific embodiment, the at least one urea transporter is at least one UT-A transporter selected from a UT-A1 isoform, UT-A2 isoform, UT-A3 isoform, UT-A4 isoform, and UT-A5 isoform. In another specific embodiment, the at least one solute is a monosaccharide and the transporter polypeptide is a glucose transporter polypeptide, wherein the monosaccharide is selected from glucose, fructose, and galactose. In another specific embodiment, in the monosaccharide is glucose, and the glucose transporter is selected from GLUT1, GLUT2, GLUT3, and GLUT4. In further particular embodiments, the indicator cell is a red blood cell.

In another embodiment of the method of identifying an agent that inhibits transport of a neutrally charged solute across a cell membrane of a cell, the at least one solute is a glycerol and the transporter polypeptide is an aquaporin that is capable of transporting glycerol and water across a cell membrane, wherein the aquaporin is selected from AQP3, AQP7, and AQP9. In certain specific embodiments, the indicator cell further comprises an aquaporin that is capable of transporting water and is incapable of transporting glycerol, wherein the aquaporin is selected from AQP0, AQP1, AQP2, AQP4, AQP5, AQP6, and AQP8. In this embodiment, the first level of indicator cell lysis indicates lysis of 41% to 100% of the indicator cells in the first substantially isosmolar mixture, and the second level of indicator cell lysis indicates lysis of 0% to 40% of the indicator cells in the second substantially isosmolar mixture.

In certain particular embodiments of the methods described above and herein, when the indicator cell is a red blood cell, the first level of indicator cell lysis and the second level of indicator cell lysis are determined by spectrophotometry. In one particular embodiment, spectrophotometry comprises measuring absorbance at 710 nm.

In another embodiment, provided herein is a method of identifying an agent that inhibits transport of urea across a cell membrane, which method comprises (a) preparing a first indicator cell suspension and a second indicator cell suspension, wherein each of said first and second indicator cell suspensions comprises one or a plurality of cells suspended in a first solution that comprises urea or an analogue thereof in an amount sufficient to provide a hyperosmolar solution, the indicator cells being derived from a biological sample and each comprising at least one urea transporter polypeptide; (b) contacting a candidate agent with the first indicator cell suspension of (a) under conditions and for a time sufficient for the candidate agent to interact with the at least one urea transporter polypeptide of the indicator cell; (c) subsequent to step (b), diluting the first indicator cell suspension with a second solution to obtain a first substantially isosmolar mixture and diluting the second indicator cell suspension with the second solution to obtain a second substantially isosmolar mixture; and (d) comparing a first level of indicator cell lysis in the first substantially isosmolar mixture to a second level of indicator cell lysis in the second substantially isosmolar mixture, wherein the agent inhibits urea transport across a cell membrane if the first level of indicator cell lysis is greater than the second level of indicator cell lysis. In one specific embodiment, the indicator cell endogenously expresses the at least one urea transporter polypeptide. Alternatively, the indicator cell comprises an exogenous polynucleotide that encodes the at least one urea transporter polypeptide, and that directs expression of the at least one urea transporter polypeptide in the indicator cell. In particular embodiments, the at least one urea transporter is a UT-B transporter, and in other particular embodiments, the at least one urea transporter is at least one UT-A transporter selected from a UT-A1 isoform, a UT-A2 isoform, a UT-A3 isoform, a UT-A4 isoform, and a UT-A5 isoform. In certain embodiments, the solute is selected from urea, a urea analogue, a monosaccharide, and a disaccharide, wherein the urea analogue is selected from formamide, acetamide, propionamide, N-methylurea, butyramide, and isobutyramide. In other particular embodiments, the indicator cell is a red blood cell. In certain embodiments, the candidate agent is a member of a combinatorial library, and in particular embodiments, the candidate agent is a small molecule. In specific embodiments, the first level of indicator cell lysis indicates lysis of 41% to 100% of the indicator cells in the first substantially isosmolar mixture and the second level of indicator cell lysis indicates lysis of 0% to 40% of the indicator cells in the second substantially isosmolar mixture. In particular embodiments, the solute is a urea analogue and the hyperosmolar solution comprises the urea analogue at a concentration of 1.0-1.5 M, wherein in certain embodiments, the urea analogue is acetamide or N-methylurea. In a more specific embodiment, the indicator cell is a murine red blood cell and the solute is N-methylurea, and in another specific embodiment, the indicator cell is a human red blood cell and the solute is acetamide. In one embodiment, when the solute is urea and the hyperosmolar solution comprises 2.0-3.0 M urea, the first level of indicator cell lysis indicates lysis of 41% to 100% of the indicator cells in the first substantially isosmolar mixture, and the second level of indicator cell lysis indicates lysis of 0% to 40% of the indicator cells in the second substantially isosmolar mixture.

Also provided herein is a method of identifying an agent that inhibits transport of water across a cell membrane, comprising: (a) preparing a first indicator cell suspension and a second indicator cell suspension, wherein each of said first and second indicator cell suspensions comprises one or a plurality of cells suspended in a first solution that comprises a neutrally charged solute in an amount sufficient to provide a hyperosmolar solution, the indicator cells being derived from a biological sample and each comprising at least one aquaporin polypeptide; (b) contacting a candidate agent with the first indicator cell suspension of (a) under conditions and for a time sufficient for the candidate agent to interact with the at least one aquaporin polypeptide of the indicator cell; (c) subsequent to step (b), diluting the first indicator cell suspension with a second solution to obtain a first substantially isosmolar mixture and diluting the second indicator cell suspension with the second solution to obtain a second substantially isosmolar mixture; and (d) comparing a first level of indicator cell lysis in the first substantially isosmolar mixture to a second level of indicator cell lysis in the second substantially isosmolar mixture, wherein the agent inhibits water transport across a cell membrane if the first level of indicator cell lysis is less than the second level of indicator cell lysis. In one specific embodiment, the indicator cell endogenously expresses the at least one aquaporin polypeptide. Alternatively, the indicator cell comprises an exogenous polynucleotide that encodes the at least aquaporin polypeptide, and that directs expression of the at least one aquaporin polypeptide in the indicator cell. In certain embodiments, the at least one aquaporin (AQP) polypeptide is selected from AQP1, AQP2, AQP3, and AQP4. In other particular embodiments, the indicator cell is a red blood cell. In certain embodiments, the candidate agent is a member of a combinatorial library, and in particular embodiments, the candidate agent is a small molecule. In certain embodiments, the solute is selected from urea, a urea analogue, a monosaccharide, and a disaccharide, wherein the urea analogue is selected from formamide, acetamide, propionamide, N-methylurea, butyramide, and isobutyramide. In one embodiment, when the solute is urea and the hyperosmolar solution comprises 2.5-5.0 M urea, the first level of indicator cell lysis indicates lysis of 0% to 41% of the indicator cells in the first substantially isosmolar mixture, and the second level of indicator cell lysis indicates lysis of 41% to 100% of the indicator cells in the second substantially isosmolar mixture. In another specific embodiment, when the solute is a urea analogue, the hyperosmolar solution comprises the urea analogue at a concentration of 2.0-3.5 M. In still another specific embodiment, the solute is glucose and the hyperosmolar solution comprises glucose at a concentration of 2.0-3.5 M. In these embodiments, the first level of indicator cell lysis indicates lysis of 0% to 41% of the indicator cells in the first substantially isosmolar mixture, and the second level of lysis determined indicates lysis of 41% to 100% of the indicator cells in the second substantially isosmolar mixture.

Also provided herein in another embodiment, is a method of identifying an agent that inhibits transport of a neutrally charged solute across a cell membrane, which method comprises (a) preparing a first indicator cell suspension and a second indicator cell suspension, wherein each of said first and second indicator cell suspensions comprises one or a plurality of cells suspended in a first solution that comprises a neutrally charged solute in an amount sufficient to provide a hyperosmolar solution, the indicator cells being derived from a biological sample and each comprising at least one transporter polypeptide that is capable of transporting the solute across a cell membrane; (b) contacting a candidate agent with the first indicator cell suspension of (a) under conditions and for a time sufficient for the candidate agent to interact with the at least one transporter polypeptide of the indicator cell; (c) subsequent to step (b), diluting the first indicator cell suspension with a second solution to obtain a first substantially isosmolar mixture and diluting the second indicator cell suspension with the second solution to obtain a second substantially isosmolar mixture; and (d) comparing a first level of indicator cell lysis in the first substantially isosmolar mixture to a second level of indicator cell lysis in the second substantially isosmolar mixture, wherein the agent inhibits transport of the solute across a cell membrane if the first level of indicator cell lysis is greater than the second level of indicator cell lysis. In one particular embodiment, the solute is urea or an analogue thereof and the transporter polypeptide is a urea transporter polypeptide, wherein the urea analogue is selected from formamide, acetamide, propionamide, N-methylurea, butyramide, and isobutyramide. In a specific embodiment, the solute is urea and the at least one transporter polypeptide is a UT-B transporter, and in another specific embodiment, the solute is urea and the at least one transporter polypeptide is at least one UT-A transporter selected from a UT-A1 isoform, a UT-A2 isoform, a UT-A3 isoform, a UT-A4 isoform, and a UT-A5 isoform. In still another specific embodiment, the solute is a monosaccharide and the transporter polypeptide is a glucose transporter polypeptide, wherein the monosaccharide is from glucose, fructose, or galactose, and wherein the glucose transporter is selected from GLUT1, GLUT2, GLUT3, and GLUT4. In certain embodiments, the indicator cell is a red blood cell.

In certain particular embodiments of the methods described above and herein, when the indicator cell is a red blood cell, the first level of indicator cell lysis and the second level of indicator cell lysis are determined by spectrophotometry. In one particular embodiment, spectrophotometry comprises measuring absorbance at 710 nm.

Also provided herein in another embodiment, is a method for treating a disease or disorder associated with a fluid retention imbalance comprising administering to a subject a composition comprising a pharmaceutically suitable excipient and a compound that inhibits transport of a neutrally charged solute by a solute transporter across a cell membrane. In certain embodiments, the disease or disorder is selected from a cardiovascular disease, syndrome of inappropriate antidiuretic hormone secretion (SIADH), cirrhosis, azotemia, acute renal failure, chronic renal insufficiency, fluid retention, diabetes, and abnormal uresis. In a particular embodiment, the neutrally charged solute is urea and the transporter is a urea transporter.

In another embodiment, a method is provided for treating a disease or disorder associated with a fluid retention imbalance comprising administering to a subject a composition comprising a pharmaceutically suitable excipient and a compound that inhibits transport of water by an aquaporin across a cell membrane. In certain embodiments, the disease or disorder is selected from a cardiovascular disease, syndrome of inappropriate antidiuretic hormone secretion (SIADH), cirrhosis, azotemia, acute renal failure, chronic renal insufficiency, fluid retention, diabetes, and abnormal uresis.

Also provided herein is a method for treating a disease or disorder associated with a urea clearance insufficiency comprising administering to a subject a composition comprising a pharmaceutically suitable excipient and a compound that inhibits transport of urea by a urea transporter across a cell membrane.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells and equivalents thereof known to those skilled in the art, and so forth. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

BRIEF DESCRIPTION OF THE DRAWINGS

FIG. 2(A) demonstrate the effect of acetamide concentration on RBC osmotic lysis. Human RBC suspensions, loaded with indicated concentrations of acetamide, were diluted in acetamide-free buffer in the absence (open circles) or presence of 0.7 mM phloretin (closed circles). RBC lysis was assayed by absorbance at 710 nm ($O.D._{710}$) (±SE, 4 wells per condition). The dashed line indicates the conditions chosen for high-throughput screening. FIG. 2(B) presents a frequency histogram of $O.D._{710}$ values for positive and negative controls from eight 96-well plates, with z'-value shown.

FIG. 6A illustrates concentration-inhibition curves for indicated compounds (structures shown in FIG. 5A) determined by light scattering in response to a 100-mM inwardly directed urea gradient. RBCs were incubated for 5 minutes with compounds at indicated concentrations prior to stopped-flow measurements. FIG. 6B shows numerically simulated inhibitor concentration-dependence used to determine $EC_{50}$ from stopped-flow experiments as in FIG. 6A. The inverse of normalized cell volume, $V_o/V(t)$, is plotted to approximate the light-scattering data at the indicated percentages of urea transport inhibition. FIG. 6C illustrates the membrane sidedness of UT-B inhibition. Experiments were performed as described for FIG. 6A and in the Examples, except that inhibitors (0.1 µM $urea_{inh}$-101 and 0.05-0.2 µM $urea_{inh}$-302) added only to the urea-containing solution (250 mM urea+PBS) where indicated. FIG. 6D illustrates the reversibility of UT-B inhibition. Where indicated, inhibitors (0.1 µM $urea_{inh}$-101 and 0.4 µM $urea_{inh}$-302) were washed out following a 10 min incubation, prior to stopped-flow measurements.

FIG. 7A illustrates dose-inhibition relationships for $urea_{inh}$-101 (left) and $urea_{inh}$-302 (right) against mouse UT-B determined by stopped-flow light scattering measurements performed using wild-type mouse RBCs in response to a 100-mM inwardly directed gradient of N-methylurea. FIG. 7B shows UT-A1-mediated urea flux in stably transfected MDCK cells. Cells were treated (open circles and open triangles) or not treated (closed circles) with 10 µM forskolin. Where indicated, phloretin (0.7 mM) was present (open triangles) (±SE, 3 filters per condition). The dashed line indicates the time chosen (15 min) to evaluate UT-A1 inhibition as shown in FIG. 7C. FIG. 7C illustrates concentration-dependent inhibition of mouse UT-B (triangles) and rat UT-A1 (circles) by urea$_{inh}$-101 (closed symbols) and urea$_{inh}$-302 (open symbols), determined from data obtained from experiments as in FIGS. 7A and 7B.

FIG. 8A presents representative traces of mouse RBC water permeability performed at 10° C., with genotypes and conditions indicated. Inhibitors urea$_{inh}$-201 and urea$_{inh}$-302 were used at 25 μM. FIG. 8B presents osmotic water permeability coefficients ($P_f$) from experiments as illustrated in FIG. 8A (±SE, 3-7 curves per group of RBCs pooled from 4 mice per genotype). *, P<0.01 compared with no inhibitor; #, P<0.01 compared with wild-type (no inhibitor).

DETAILED DESCRIPTION OF THE INVENTION

Figure 1:
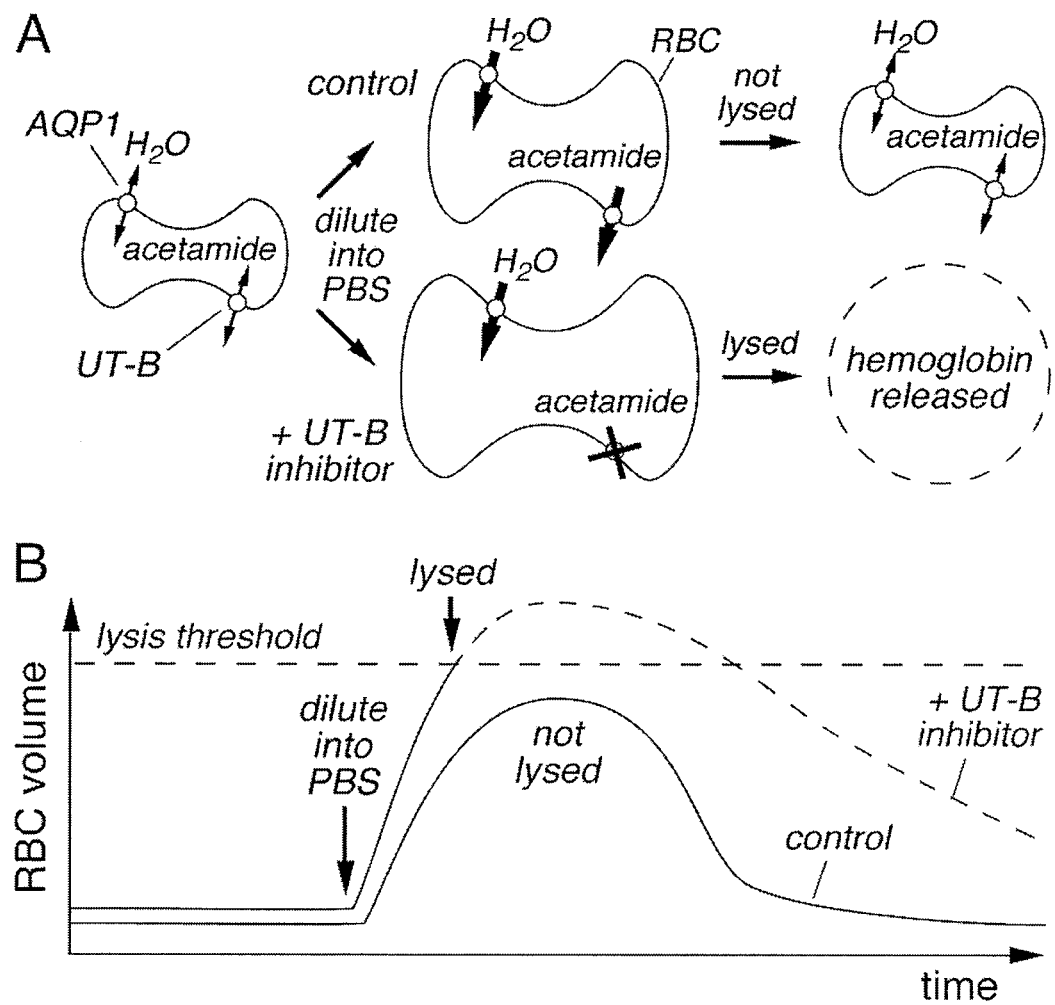
FIGS. 1A and 1B illustrate an erythrocyte osmotic lysis assay for identifying inhibitors of urea transporters. (A) The schematic represents human RBCs that express water and urea channels (AQP1 and UT-B, respectively) and that are preloaded with urea or a urea analog, such as acetamide. Following replacement of the external hyperosmolar buffer with an urea/acetamide-free isosmolar solution, water entry results in cell swelling, which is limited by UT-B-mediated urea/acetamide efflux. Under optimized assay conditions, UT-B-facilitated urea/acetamide transport prevents osmotic lysis (top), whereas UT-B inhibition impairs urea/acetamide exit resulting in substantial lysis (bottom). (B) The graph illustrates biphasic cell volume changes in the lysis assay. Increased RBC volume beyond a threshold results in lysis. The dashed curve shows the hypothetical time course of RBC volume if lysis had not occurred.

Provided herein are rapid and reproducible methods of identifying and characterizing potent, specific agents that alter the volume of a cell, particularly agents that alter the transport of small, neutrally charged solutes (i.e., lipid-insoluble nonelectrolytes) across a cell membrane and agents that alter transport of water across a cell membrane. The agents thus identified may be useful for treating diseases, disorders, and conditions related to aberrant transport of water and/or aberrant transport of small neutrally charged solutes. Examples of such diseases, disorders, and conditions include diabetes, conditions related to renal insufficiency, hypertension, fluid retention, cirrhosis, azotemia, acute renal failure, syndrome of inappropriate antidiuretic hormone secretion (SIADH), and other renal, cardiovascular, and metabolic diseases and disorders.

The amount of water in the various compartments of a cell is controlled physiologically by homeostasis. To maintain osmotic homeostasis, water is rapidly equilibrated across a cell membrane. Transmembrane proteins called aquaporins facilitate transport of water across cell membranes. Another process important to maintaining homeostasis of cell and body fluid compartments is transport, or movement, of small, neutrally charged (hydrophilic, lipid insoluble) molecules across cell membranes. Specific transmembrane transport proteins selectively transport small, lipid-insoluble molecules across cell membranes. As noted above, certain diseases, disorders, and pathological conditions are related to, are caused by, or result from aberrant transport of water or a small, neutrally charged solute or both.

The methods described herein have value in high throughput screening, that is, in automated screening of a large number of candidate agents that alter transport of a small, neutrally charged solute or water in one or more cell types. The method may be used to screen synthetic or natural product libraries for bioactive agents. The methods described herein are therefore amenable to automated, cost-effective high throughput drug screening and have immediate application in a broad range of pharmaceutical drug development programs. In one embodiment, the agents to be screened are organized in a high throughput screening format such as using microfluidics-based devices, or a 96-well plate format, or other regular two dimensional array, such as a 384-well, 48-well or 24-well plate format, or an array of test tubes. The format is therefore amenable to automation. An automated apparatus that is under the control of a computer or other programmable controller may be used for one or more steps of the methods described herein. A controller can monitor the results of each step of the process and can automatically alter the testing paradigm in response to those results.

Methods

In one embodiment, the methods are provided that identify agents that alter the volume of a cell. Methods described herein employ osmotic lysis and are readily amenable to automated, cost-effective high-throughput screening of large combinatorial libraries of agents, drugs, and pharmacophores to identify and characterize lead compounds. These methods may be performed more rapidly and are technically simpler than the methods that measure kinetics of water and/or solute transport in a cell. The methods exploit two opposing transport processes in cells, water transport and solute transport (e.g., urea or glucose transport). These methods, which are described in greater detail herein, include steps of exposing cells to a high concentration, outwardly directed gradient of a solute in a hyperosmolar solution for a time sufficient to cause the volume of the cells to decrease. The hyperosmolar mixture of cells is then diluted into another solution, in which the solute is absent or at a significantly lower concentration than in the hyperosmolar solution, to obtain a substantially isosmolar mixture. The rapid change in the osmolarity of the mixture causes a rapid influx of water such that complete or partial lysis of the cells occurs (i.e., a disruption of the integrity of the outer cell membrane), which can be determined by any number of techniques known in the art and described herein. Thus, agents that inhibit transport of a neutrally charged solute across a cell membrane are detected by observing an increase in cell lysis compared to a control sample that does not contain the agent. An agent that inhibits transport of water by an aquaporin protects the cell from lysis, and is thus detected by observing a decrease in cell lysis compared with a control sample that does not contain the agent.

Small, neutrally charged molecules referred to herein are, in general, lipid insoluble and hydrophilic, and include (but are not limited to) urea and analogues thereof, glycerol, monosaccharides (e.g., glucose, fructose, galactose, and ribose), and disaccharides. In one embodiment, methods are provided for identifying agents that alter (i.e., increase or decrease in a statistically significant or biologically significant manner) the volume of a cell. In a specific embodiment, the methods described herein may be used for identifying agents that alter (i.e., increase or decrease in a statistically significant or biologically significant manner) transport of a small, neutrally charged solute across a cellular membrane. In yet another embodiment, methods are provided that identify agents that alter (i.e., increase or decrease in a statistically significant or biologically significant manner) transport of water across a cell membrane. Transport across a cellular membrane includes transport of a solute, as described herein, or water across the outer cell membrane from the extracellular space or environment into the cell (i.e., influx) and includes transport of a solute or water out of the cell into the extracellular space (i.e., efflux). In particular embodiments, the methods described herein identify agents that alter water permeability or urea permeability of a cell. In other certain embodiments, a cellular membrane refers to a membrane of an organelle, such as a mitochondrion, an organelle that also can change in volume as water and/or solutes traverse the mitochondrial membrane.

In a specific embodiment, a method of identifying and characterizing urea transporter (UT) inhibitors is provided that leads to the discovery of potent, specific, small molecule inhibitors of UTs. Previously, the only available UT inhibitors included compounds that were nonspecific and exhibited moderate or low activity, which include for example, the non-specific membrane intercalating agent phloretin (exhibiting activity at >0.5 mM); urea analogs such as thiourea, methylurea, and dimethylurea (exhibiting activity at 50-100 mM); (see, e.g., Mayrand et al., supra), and chemically modified urea analogs (exhibiting irreversible activity at 30-100 µM) (Martial et al., *Pflügers Arch.* 423:51-58 (1993)). The method described herein was used to discover and characterize UT inhibitors that are drug-like small molecules with high chemical diversity and high affinity.

An agent may alter transport of water or a neutrally charged solute either directly or indirectly. An agent that directly alters transport of a solute by a specific solute transporter or that alters transport of water by an aquaporin includes an agent that directly interacts with or binds to the transporter and thus alters (i.e., increases or decreases in a statistically significant or biologically significant manner) the capability of the transporter to transport its substrate (i.e., a solute or water). Particularly useful agents include agents that inhibit or block the capability of a solute transporter to transport its specific solute or agents that inhibit or block the capability of an aquaporin to transport water.

The agents identified by the methods described herein may interact specifically with a family of solute transporters. For example, an agent may interact with the family of urea transporters, which includes both UT-A and UT-B transporters. Alternatively, the agent may act specifically with a subfamily (or class) of a transporter family; for example, an agent may interact with UT-A transporters but not interact specifically with UT-B transporters. Agents may be identified that interact with at least one member of a subfamily but not all members of the subfamily. For example, an agent may act with at least one, at least two or more, but not all UT-A isoforms, which include UT-A1, UT-A2, UT-A3, UT-A4, UT-A5, and UT-A6. Similarly, agents may be identified by the methods described herein that interact with all transporters in the family of glucose transporters. Other agents identified may interact with at least one, or at least two or more, but not all glucose transporters; for example, an agent may be identified that interacts with at least one of GLUT1, GLUT2, GLUT3, and GLUT4. The methods described herein may also be used to identify agents that interact with each member of the family of water transporters (i.e., aquaporins), or the methods described herein may be used to identify agents that interact with at least one, at least two or more but not all aquaporin polypeptides.

In a specific embodiment, a method is provided for identifying agents that alter transport of urea by at least one urea transporter (UT) (i.e., alter urea permeability of a cell). In a more specific embodiment, methods are provided to identify agents that inhibit (i.e., block, prevent, interfere with, abrogate, or decrease) transport of urea by at least one urea transporter (UT) polypeptide. In another specific embodiment, the methods may be used to identify agents that alter transport of glucose by at least one glucose transporter. In yet a more specific embodiment, methods are provided to identify agents that inhibit (i.e., block, prevent, interfere with, abrogate, or decrease) transport of glucose by at least one glucose transporter polypeptide. In another particular embodiment, the methods are provided herein to identify agents that alter transport of water by at least one aquaporin across a cell membrane (i.e., alter water permeability of a cell). In a more particular embodiment, methods are provided to identify agents that inhibit the capability of at least one aquaporin to transport water across a cell membrane.

In one embodiment, a method of identifying an agent that alters the volume of a cell, comprises contacting, exposing, mixing, suspending, or placing an indicator cell or a plurality of indicator cells, or a biological sample that contains an indicator cell or a plurality of indicator cells, with a first solution, which comprises at least one neutrally charged solute in an amount sufficient to provide a hyperosmolar solution. The mixture, suspension, composition, sample, or combination of indicator cells in the hyperosmolar solution is contacted with (i.e., combined with, mixed with, or in some manner permitted to interact with) a candidate agent under conditions and for a time sufficient for the candidate agent to interact with the indicator cells. The osmolarity of the solution containing the indicator cells is then reduced to obtain a substantially isosmolar solution. The mixture, suspension, composition, sample, or combination of indicator cells in the hyperosmolar solution (with or without the candidate agent) is then added to (i.e., diluted into, combined with, replaced by) a second solution (e.g., a physiological buffer, diluent, or media) to obtain a substantially isosmolar mixture. The second solution lacks the at least one neutrally charged solute or the second solution comprises a significantly lower concentration of the at least one neutrally charged solute. For example, the hyperosmolar solution may be replaced if the cells are adherent cells, by removing the hyperosmolar solution and then adding an isosmolar solution to the container comprising the adherent cells. If the indicator cells are in suspension, the hyperosmolar solution may be diluted by the addition of a second solution that lacks the neutrally charged solute. The hyperosmolar mixture, suspension, composition, sample, or combination of cells is added to a sufficient volume of the isosmolar solution to immediately and rapidly change the osmolarity of the hyperosmolar mixture, suspension, composition, sample, or combination to a substantially isosmolar mixture, suspension, composition, sample, or combination. In other words, the adjustment in osmolarity of the hyperosmolar solution comprising the indicator cells to a substantially isosmolar solution comprising the indicator cells need not be accomplished gradually or slowly over time.

To determine whether a candidate agent alters the volume of a cell, the level of indicator cell lysis in the substantially isosmolar mixture, suspension, composition, sample, or combination of indicator cells in the presence of the candidate agent (i.e., also called herein a first level of indicator cell lysis) is compared with a second level of indicator cell lysis, which is the level of lysis of the indicator cell in a control sample that is not contacted with a candidate agent. The level of lysis of indicator cells in control samples that lack the candidate agent is typically determined in parallel and concurrently with determining the level of lysis of indicator cells in the samples containing a candidate agent. In certain instances, the level of indicator cell lysis in the control samples that lack the candidate agent may be determined prior to analysis of samples containing a candidate agent. The number of control samples included in the method, the composition of control samples (i.e., including or excluding certain components, such as an agent or composition that is known to be capable of altering transport of a solute or water across a cell membrane (i.e., positive control)), and the time at which the control samples are prepared and evaluated are described herein and can also be readily deter mined by a person skilled in the assay method art.

Osmolarity is a measure of osmoles of a solute per liter of solution, and osmolality is a measure of moles of a solute per kilogram of solvent. An osmole is a unit of measure that defines the number of moles of a solute in a solution that contributes to the osmotic pressure of the solution. For example, a mole of glucose in a solution or a mole of urea in a solution is one osmole of glucose or urea. However, for certain solutes that dissociate in a solution into two or more ions, the osmolarity is commensurate with the number of ions. For example, a mole of sodium chloride in a solution is two osmoles because sodium chloride has one mole of sodium ion and one mole of chlorine ion, and sodium chloride will dissociate into a sodium ion and a chloride ion in a solution. Osmotic pressure (also called osmotic potential) is the hydrostatic pressure exerted by a solution across a perfect semi-permeable membrane (i.e., one which allows free passage or diffusion of water and completely prevents movement of a solute) due to a differential in the concentration of the solutes, that is the force exerted to induce water flow. Water flows from a low osmolarity to a high osmolarity at a rate directly proportional to the difference (gradient) in osmolarity.

Use of terms such as hyperosmolar and hyposmolar, implies comparison between two solutions or between two fluid compartments. By way of example, one fluid compartment may be intracellular, and the second fluid compartment may be the extracellular space. Thus, when indicator cells are placed in a solution made hyperosmolar by the presence of a particular solute (e.g., urea, a urea analogue, or a monosaccharide such as glucose), the concentration of a solute or solutes is greater than the intracellular concentration of the solute(s), and water in cells that are placed in a hyperosmolar solution will flow out of the cell, which in turn, results in the volume of the cell decreasing. When the hyperosmolar solution containing the cells in then diluted into or replaced by a solution in which the solute is at a significantly lower concentration than in the hyperosmolar solution or the solute is absent, thus exposing the cells to a substantially isosmolar solution, water flows into the cell. In the absence of an inhibitor of solute transport, the opposing process that occurs is the transport of the solute out of the cell by at least one transporter capable of transporting the solute. As used herein, the flow or movement of water across a cell membrane in the indicator cells includes facilitated transport of water by at least one aquaporin and does not solely result from simple diffusion of water across a cell membrane.

The osmolality of a solution that contains more than one solute may be determined empirically by methods known in the art and described herein, that measure colligative properties of solutions (i.e., properties that are independent of the nature of the particle and are dependent only on the concentration of solute particles in a solution). A commonly used method for determining osmolality is freezing point depression osmometry. The freezing point depression is the difference between the freezing point of a pure solvent and the solvent that contains a solute, and therefore is directly proportional to the molal concentration of the solution. Instruments that measure freezing point depression are commercially available. Osmolality of solutions may also be determined by measuring other colligative properties, such as osmotic pressure, depression of vapor pressure, and elevation of boiling point using methods and techniques practiced in the art.

Provided herein are methods of identifying an agent that alters the volume of a cell. In one embodiment, a first indicator cell sample is prepared and a second indicator cell sample is prepared, wherein each of the first and second indicator cell samples comprises one or a plurality of indicator cells combined with a first solution that comprises a neutrally charged solute in an amount sufficient to provide a hyperosmolar solution, wherein the indicator cells are derived from a biological sample. Exemplary solutes include urea; a urea analog (e.g., formamide, acetamide, propionamide, N-methylurea, butyramide, and isobutyramide); glycerol; a monosaccharide (e.g., glucose, fructose, galactose, ribose); or a disaccharide. The hyperosmolar solution includes a physiological solvent that is an appropriate diluent or media for the particular cells and includes the solute or an analogue of the solute (i.e., a compound that is structurally and chemically similar to the solute) at a concentration sufficient that upon exposure of the indicator cells to the hyperosmolar solution, the volume of the indicator cell decreases due to the flow of water out of the cell (efflux).

The indicator cells may be combined with the hyperosmolar solution in any of a variety of containers or sample vessels, including test tubes, multi-well plates such as 48-well, 72-well, 96-well plates, 384-well plates or other such vessels, including those useful for high throughput screening formats wherein, for example, detection of indicator cell lysis in a plurality or reaction vessels may be automated. The cells may be in suspension or adhered to a surface. When cells are adherent cells, the surface to which the cells are adhered may be solid, such as a tissue culture plate (e.g., 24-well, 48-well, 72-well, 96-well plates, 384-well plate), or the cells may be adhered to microcarrier beads. Alternatively, the surface on which the cells adhere may be porous such that the apical cell surface and basolateral cell surface may be exposed to or bathed in the solutions described herein.

The number of samples to be assayed may influence the degree of automation that can be implemented. For example, when high throughput screening, (i.e., assaying a large number of samples in a relatively brief time period) is desired, robotic or semi-robotic instruments may be used. In certain instances, microfluidics multiplexing technologies may be employed (see, e.g., Thorsen et al., Science 298:580-84 (2002); Manz and Becker, eds. *Microsystem Technology in Chemistry and Life Sciences* (Springer 1999); Zhang et al, *Microelectrofluidic Systems: Modeling and Simulation* (CRC Press 2002); Tabeling, *Introduction to Microfluidics* (Oxford University Press 2006); U.S. Pat. Nos. 6,969,850; 6,878,755; 6,454,924; 6,681,788; 6,284,113). Alternatively, samples may be processed manually, even for formats that accommodate large sample numbers (e.g., 96-well microplates).

Each vessel, tube, or well (herein referred to as sample) of indicator cells is maintained in (i.e., exposed to, placed in, combined with, or incubated in) the hyperosmolar solution under conditions and for a time sufficient for the volume of the cell to decrease due to the directional flow of water out of the cell. Conditions for maintaining or incubating the indicator cells in a hyperosmolar solution include, for example, temperature; agitation and speed of agitation or other methods of maintaining the cells in suspension if the cells are suspension cells (that is, cells that are not adhered to a surface, vessel, container, or multi-well plate); atmosphere (for example, the indicator cells may be a cell that requires an atmosphere containing carbon dioxide at a level typical for maintaining viability of cultured cells); and other conditions with which a person skilled in the art will be familiar.

The conditions and the period of time that the indicator cells are incubated in the hyperosmolar solution can be determined empirically for the type of indicator cell that is used. The temperature at which the cells may be incubated in the hyperosmolar solution may be a temperature or a range of temperatures considered ambient room temperature (e.g., between approximately 19° C.-26° C. or between approximately 21° C.-25° C.) or may be a temperature or range of temperatures considered physiological for animal cells (e.g., 37° C. or any temperature between 35° to 40° C.). Generally, the cells are placed in a hyperosmolar solution for at least 15 minutes, at least 30 minutes, at least 60 minutes (1 hour), at least 90 minutes, or at least 120 minutes (2 hours), or at least 180 minutes (3 hours), or at least 240 minutes (4 hours), or longer than 4 hours. By way of example, if the indicator cells are red blood cells, the cells may be placed in the hyperosmolar solution for 30 minutes to 120 minutes.

To a sample of indicator cells in a hyperosmolar solution may be added at least one candidate agent. In certain instances, such as when the methods described herein are used for screening a library with thousands of agents, at least two, three, four, or more candidate agents may be added to the indicator cells in a hyperosmolar solution. At least one subsequent assay may be performed, whereby the candidate agents that were added together in a single sample of indicator cells in the hyperosmolar solution in a first assay may then be contacted separately with indicator cells. The indicator cells and the candidate agent are permitted to interact (i.e., by combining, mixing, contacting) under conditions and for a time sufficient for the candidate agent to interact with the indicator cell, and particularly to interact with a solute transporter or aquaporin of the indicator cell. Persons skilled in the art will appreciate that appropriate conditions to permit interaction between the candidate agent and the indicator cell include temperature; agitation and speed of agitation or other methods of maintaining contact between the indicator cells and the candidate agent; and atmosphere; and the like as described herein. The kinetics of binding of a transporter and an agent that alters the capability of a solute transporter to transport the solute may be rapid. Thus, in certain instances, the time sufficient for an indicator cell and candidate agent to interact may be 1-2 minutes, 3-4 minutes, 5-6 minutes, 7-8 minutes, or 9-10 minutes. In other instances, the time sufficient may be at least 10, 15, 20, 25, or 30 minutes or longer than 30 minutes.

After a sufficient time for the indicator cell and the candidate agent to interact, the osmolarity of the sample is decreased to place the indicator cells in a substantially isosmolar solution. The osmolarity of the sample may be reduced by removing the hyperosmolar solution and replacing the hyperosmolar solution with a second solution (e.g., a physiological buffer, diluent, or media) that lacks the neutrally charged solute or that has a significantly reduced number of osmoles of the solute compared with the hyperosmolar solution, such that a mixture, suspension, or sample of the indicator cells in an isosmolar solution is obtained. Alternatively, the hyperosmolar mixture, combination, or sample of the indicator cells (in the absence and presence of the candidate agent) is diluted into a second solution (e.g., a physiological buffer, diluent, or media) to obtain a substantially isosmolar mixture. The percent dilution or fold-dilution of the hyperosmolar solution to provide a substantially isosmolar mixture may also be determined empirically for a particular type of indicator cell, and is the fold-dilution sufficient to observe an increase in the volume of the indicator cell as water flows into the cell. The osmoles in a substantially isosmolar mixture may be reduced at least ten fold compared with the osmoles of the hyperosmolar solution. For example, if the hyperosmolar is 1500 mOsm, the substantially isosmolar mixture may be about 150 mOsm. In certain embodiments, the osmoles in a substantially isosmolar mixture may be reduced between seven, eight, nine, or ten fold compared with the osmoles in the hyperosmolar solution. In other certain embodiments, the osmoles in a substantially isosmolar mixture may be reduced 11-12-, 13-, 14-, 15-, 16-, 17-, 18-, 19-, 20-fold or greater compared with the osmoles in the hyperosmolar solution.

To determine whether the interaction of the candidate agent with the cell alters the volume of the indicator cells, the level of lysis of the indicator cells in the substantially isosmolar solution in the absence and presence of the agent is determined. Lysis as used herein refers to complete or total lysis of a cell (i.e., complete and total disruption or loss of outer cell membrane integrity) or partial lysis of the cell (i.e., partial or incomplete disruption of the outer cell membrane integrity). The loss of integrity of the outer cell membrane, whether partial or complete, can be quantified using techniques practiced in the art and described herein.

The level of cell lysis may be determined by assessing the release of an intracellular molecule, which may be detected by methods that detect a structural or functional feature of a specific intracellular molecule, such as by detecting specific binding of the intracellular molecule to an antibody or other specific ligand, or by measuring an enzymatic activity of the intracellular molecule. Release of an intracellular or cytoplasmic polypeptide or other molecule means that the polypeptide or other cellular molecule that is typically intracellular (i.e., located in the cytoplasm of the cell or in an organelle of the cell but not secreted under normal physiological conditions when the cell is viable and intact), can be detected extracellularly.

Accordingly, methods and techniques that may be used to determine the level of cell lysis include any number of immunoassay methods (e.g., ELISA, radioimmunoassay, immunoprecipitation) for detecting release of a cytoplasmic polypeptide or other molecule from the cell. Antibodies that specifically bind to a cellular polypeptide or other cellular molecule may be available from commercial vendors or can be prepared using methods routinely practiced by persons skilled in the art. The level of indicator cell lysis may be determined by detecting release of a specific intracellular molecule or of multiple intracellular molecules by labeling the cells with a detectable moiety prior to placing the cells in the hyperosmolar solution. Exemplary detectable moieties (which may also be called tags, reporter molecules, or labels) include a dye, radionuclide, luminescent group, fluorescent group, or biotin, or the like. Methods for labeling cells with a reporter molecule and for detecting the reporter molecule are known to, and routinely practiced by, a person skilled in the art. Cell lysis may also be determined by techniques that detect the enzymatic activity of a specific intracellular enzyme. Other methods and techniques for determining the level of cell lysis include detecting a released intracellular molecule or molecules by methods that include mass spectrometry, chromatography (e.g., affinity chromatography wherein a ligand of an intracellular molecule is attached to a chromatography matrix), and spectrophotometry.

Spectrophotometric measurements may be determined at a wavelength in the visible or ultraviolet spectrum. In one embodiment, the level of lysis of indicator cells, such as lysis of red blood cells, can be quantified by determining the absorbance at 710 nm of a sample (Mazeron et al. *Photochem. Photobiol.* 72:172-78 (2000); Cohn et al., *Mol. Biochem. Parasitol.* 132:27-34 (2003)). Absorbance at 710 nm decreases as lysis of red blood cells increases. Thus, a sample that contains an inhibitor of a solute transporter, which has an increased level of red blood cell lysis compared to a sample that does not contain a solute transporter inhibitor, exhibits a decreased level of absorbance at 710 nm compared with a control sample (i.e., in the absence of an inhibitor).

Other techniques for quantifying lysis of cells may be specific for one or more different types of indicator cells. For example, when the indictor cells are red blood cells, cell lysis may be quantified by quantifying hemoglobin, which may be accomplished spectrophotometrically, by chemical methods, or by any number of immunoassays practiced in the art. Additional exemplary methods for detecting red blood cell lysis include quantifying ATP that is released by the cell (Moehlenbrock et al., *Analyst* 131:930-7 (2006); Epub Jun. 6, 2006)); determining the level of cytoplasmic lactate dehydrogenase released, which can be measured in an enzymatic assay or in any number of immunoassays using an antibody that specifically binds to lactate dehydrogenase; or determining the level of oxygen released.

To determine whether an agent alters the volume of the indicator cell, the level of cell lysis of indicator cells that are contacted with a candidate agent (herein also called a first level of cell lysis) is compared with the level of lysis of indicator cells in the control sample that lacks the candidate agent (herein also called a second level of cell lysis). A control sample may be prepared in which all assay conditions and components are identical to those described above except that the candidate agent is omitted from the sample (i.e., indicator cells have not been contacted or combined with a candidate agent). Alternatively or in addition to such a control sample, at least one other control sample may include all the components of a sample that includes the candidate agent but instead of the candidate agent, the sample contains a compound or molecule that is known not to alter the volume of a cell. A person skilled in the art will also appreciate that the methods described herein may include additional control samples (including a sample comprising a known compound or agent that is capable of altering the volume of a cell) to evaluate and ensure the robustness, accuracy, and precision of the method.

As described herein, in one embodiment, altering the volume of an indicator cell comprises altering transport of a neutrally charged solute across a cell membrane, which may occur by altering the capability of a transporter polypeptide to transport the solute. In a particular embodiment, the methods described herein may be used to identify an agent that inhibits transport of a neutrally charged solute by a transporter across a cell membrane. The indicator cell may endogenously express transporter (i.e., the genome of the cell comprises a nucleotide sequence that encodes the transporter, which is transcribed into mRNA that is translated). Alternatively, the transporter may be recombinantly expressed in an indicator cell that comprises an exogenous polynucleotide that directs the expression of the transporter polypeptide. In a particular embodiment, the transporter is located in the outer cell membrane and is capable of transporting a solute into the cell from the extracellular environment or space (influx) and out of the cell into the extracellular environment or space (efflux).

In one embodiment, the methods described herein for identifying agents that alter the volume of a cell may be used to identify agents that alter transport of a small, neutrally charged solute by a transporter. In a particular embodiment, a method is provided for identifying an agent that inhibits (i.e., blocks, prevents, reduces, or decreases in a statistically or biologically significant manner) the capability of a transporter to transport a specific solute across a cell membrane and thus inhibits solute influx and/or efflux. An agent that inhibits the capability of a transporter to transport a specific solute may bind to the transporter such that transport of the solute into the cell from the extracellular space is inhibited, and/or the agent may bind to the transporter such that transport of the solute out of the cell into the extracellular space is inhibited.

As described herein, methods are provided for identifying an agent that inhibits transport of a neutrally charged solute across a cell membrane (or influx or efflux of the solute). The methods comprise combining, mixing, or contacting indicator cells that may be derived from, obtained from, or present in a biological sample, with a hyperosmolar solution to obtain a mixture, combination, or sample of the indicator cells in hyperosmolar conditions. The hyperosmolar solution includes a physiological solvent that is an appropriate diluent or media for the particular cells and includes the solute or an analogue of the solute (i.e., a compound that is structurally and chemically similar to the solute) at a concentration sufficient that upon exposure of the indicator cells to the hyperosmolar solution, the volume of the indicator cell decreases due to the flow of water out of the cell (efflux).

In one embodiment, the solute in the hyperosmolar solution comprises a solute or analogue thereof at a concentration of about 1.25 M or may be between about 1.0-1.5 M, between about 0.5-2.0 M, or between about 1.0-1.75 M. The concentration of the solute or analogue thereof may be optimized by titration experiments so that an agent that inhibits the capability of a transporter to transport the solute is readily distinguished (i.e., quantifiably distinguishable) from the controls.

As described herein, after placing the indicator cells in a hyperosmolar solution, at least one candidate agent is added to the hyperosmolar mixture, suspension, or sample, of indicator cells under conditions and for a time sufficient for the candidate agent to contact and interact with the indicator cells, and in particular, under conditions and a time sufficient for the candidate agent(s) to contact a solute transporter expressed by the indicator cell. The hyperosmolar mixture, sample, or suspension of cells and a candidate agent is then diluted into, or combined with, or replaced with a second solution (e.g., a physiological buffer, diluent, or media) that contains a reduced amount or totally lacks the solute of the hyperosmolar solution to obtain a substantially isosmolar mixture. The capability of the candidate agent(s) to inhibit transport of the solute by the solute transporter is then determined by comparing the level of indicator cell lysis in a sample that comprises the candidate agent(s) with the level of indicator cell lysis in a sample that lacks the candidate agent(s).

The level of lysis (partial or complete, as described herein) in indicator cells (e.g., red blood cells) in the presence of an agent (i.e., also referred to herein as a first level of lysis) that is an inhibitor of a solute transporter, is greater than the level of lysis in indicator cells that are not exposed to an inhibitor of the solute transporter (i.e., also referred to herein as a second level of indicator cell lysis). When the indicator cells in the hyperosmolar mixture comprising an active agent are transferred to, exposed to, resuspended in, placed in, or diluted into a substantially isosmolar solution, the indicator cells are incapable of transporting the solute out of the cell, thus entry of water into cells from the extracellular environment results in partial or total cell lysis. For example, in a sample that does not contain an agent or that contains an inactive agent, lysis between 0%-40%, 0%-30%, 0%-20%, 0%-15%, or 0%-10% of the indicator cells may be observed. In a sample that contains an inhibitor of a transporter, lysis of between 41%-100%, 50%-100%, 60%-100%, 70%-100%, 80%-100%, or 90%-100% of the indicator cells may be observed.

In a specific embodiment, the methods described herein and above are useful for identifying inhibitors of aquaporin polypeptides that transport both a solute such as glycerol and water (e.g., AQP3, AQP7, and AQP9). In a particular embodiment, a method is provided for identifying an agent that inhibits (i.e., blocks, prevents, reduces, or decreases in a statistically or biologically significant manner) transport of glycerol by an aquaporin across a cell membrane, and thus inhibits glycerol influx and/or efflux. Without wishing to be bound b theory, such an inhibitor that interacts with an aquaporin to inhibit transport of a solute such as glycerol would likely inhibit the capability of the transporter to transport water across a membrane. Indicator cells used in this particular embodiment, would also comprise an aquaporin that transports only water (e.g., AQP0, AQP1, AQP2, AQP4, AQP5, AQP6, and AQP8). As described herein, the indicator cells are placed in a solution that comprises a neutrally charged solute (e.g., glycerol) in an amount sufficient to provide a hyperosmolar solution. The hyperosmolar solution includes a physiological solvent that is an appropriate diluent or media for cells. After contacting the indicators cells in the hyperosmolar solution with at least one candidate agent, the hyperosmolar solution may be removed, replaced, or diluted such that the indicator cells are in a glycerol free (or solute free) medium that is substantially isosmolar. As described above, an increase in cell lysis compared to a similarly prepared sample in the absence of a candidate agent, indicates that the compound is an inhibitor of the solute-transporting aquaporin.

In certain embodiments, the solute is a monosaccharide, such as glucose, fructose, ribose, or galactose, and in other certain embodiments, the solute is a disaccharide. As described herein, the methods may be used to identify agents that alter transport of glucose across a cell membrane, including influx of glucose from the extracellular environment into the cell and efflux of glucose from the cell into the extracellular environment, by any one of the glucose transporters described herein and in the art.

In another specific embodiment, the methods described herein for identifying agents that alter the volume of a cell may be used to identify agents that alter transport of urea (or an analogue thereof) by a urea transporter, thus altering urea permeability of the cell. In a particular embodiment, a method is provided for identifying an agent that inhibits (i.e., blocks, prevents, reduces, or decreases in a statistically or biologically significant manner) transport of urea by a urea transporter across a cell membrane, and thus inhibits urea influx and/or efflux. An agent that inhibits the capability of a urea transporter to transport urea may bind to the urea transporter such that transport of urea into the cell from the extracellular space is inhibited or may bind to the urea transporter such that transport of urea out of the cell into the extracellular space is inhibited or may inhibit both influx and efflux of urea.

A method for identifying an agent that inhibits transport of urea across a cell membrane (or influx or efflux of urea) comprises preparing a mixture, suspension, or sample of indicator cells (which are obtained from or derived from a biological sample) and a hyperosmolar solution to obtain a mixture, suspension, or sample of the indicator cells in hyperosmolar conditions. The hyperosmolar solution includes a physiological solvent that is an appropriate diluent or media for cells and includes urea or a urea analog (including but not limited to formamide, acetamide, propionamide, N-methylurea, butyramide, and isobutyramide) at a concentration sufficient to result in a decrease in volume of an indicator cell due to flow of water out of the cell (efflux) when the indicator cells are placed into or incubated in the hyperosmolar solution.

In one embodiment, urea is the solute in the hyperosmolar solution. The concentration of urea in a hyperosmolar solution may be any concentration between about 2.0-3.0 M or in certain other embodiments between about 1.5-3.0 M, or between about 2.3-2.7 M. In another embodiment, the hyperosmolar solution comprises a urea analogue, which may be at a concentration of about 1.25 M or may be any concentration between about 1.0-1.5 M, or between about 0.5-2.0 M or between about 1.0-1.75 M. The concentration of urea or a urea analogue may be optimized by titration experiments so that an agent that inhibits transport of urea by a urea transporter is readily distinguished (i.e., quantifiably distinguishable) from the controls. For example, in a control sample that does not contain an agent or that contains an inactive agent, lysis of between 0%-40%, 0%-30%, 0%-20%, 0%-15%, or 0%-10% of the indicator cells (e.g., red blood cells) may be observed. In a sample that contains an inhibitor of a urea transporter, lysis of between 41%-100%, 50% to 100%, 60% to 100%, 70% to 100%, 80% to 100%, or 90% to 100% of indicator cells may be observed.

As described herein, indicator cells used in the methods for identifying agents that inhibit transport of urea by a urea transporter may include cells that endogenously express at least one urea transporter or that recombinantly express at least one urea transporter. In a particular embodiment, the indicator cells are red blood cells that endogenously express the UT-B urea transporter. The red blood cells may be obtained from any animal, including human and non-human primates, rodents, and other mammals. The solute of the hyperosmolar solution and the optimal concentration of the solute (i.e., urea or a urea analogue), may vary depending on the source of the indicator cell, which optimal concentration may be readily determined using the methods described herein. For example, in certain embodiments, the indicator cell is a human red blood cell and the hyperosmolar solution contains a urea analogue, such as acetamide. In another particular embodiment, the red blood cells are obtained from a rodent such as a mouse or a rat and the urea analogue, N-methylurea, is the solute comprising the hyperosmolar solution.

In still another embodiment, the methods described herein for identifying agents that alter the volume of a cell may be used to identify agents that alter transport of water by an aquaporin (i.e., facilitated or active transport of water by an aquaporin transporter), thus identifying an agent capable of altering water permeability of a cell. In a particular embodiment, a method is provided for identifying an agent that inhibits (i.e., blocks, prevents, reduces, or decreases in a statistically or biologically significant manner) the capability of an aquaporin to transport water across a cell membrane and thus inhibits water influx and/or efflux. An agent that inhibits transport of water across a cell membrane may bind to the aquaporin such that transport of water into the cell (influx) from the extracellular space is inhibited, or may bind to the aquaporin such that transport of water out of the cell (efflux) into the extracellular space is inhibited, or may inhibit both influx and efflux of water.

A method for identifying an agent that inhibits transport of water across a cell membrane (or influx or efflux of water) comprises preparing a mixture, suspension, or sample of indicator cells (which are obtained from or derived from a biological sample) (e.g., red blood cells) and a hyperosmolar solution to obtain a mixture, suspension, or sample of the indicator cells in hyperosmolar conditions. The indicator cell may endogenously express an aquaporin (i.e., the genome of the cell comprises a nucleotide sequence that encodes an aquaporin, which is transcribed into mRNA that is translated). For example, the indicator cells may be human red blood cells that endogenously express AQP1. Alternatively, the indicator cell may express at least one aquaporin recombinantly, that is, the indicator cell comprises an exogenous polynucleotide that encodes and directs the expression of the aquaporin polypeptide.

The hyperosmolar solution comprises a physiological solvent that is an appropriate diluent or media for cells and comprises a small, neutrally charged solute, such as urea or a urea analog (including but not limited to formamide, acetamide, propionamide, N-methylurea, butyramide, and isobutyramide), or a monosaccharide such as glucose at a concentration sufficient to result in a decrease in volume of an indicator cell due to flow of water out of the cell (efflux) when the indicator cells are placed into or incubated in the hyperosmolar solution. In certain embodiments, in the methods for identifying aquaporin inhibitors, the concentration of the solute in the hyperosmolar solution is greater than in a hyperosmolar solution that is used in the methods for identifying an agent that inhibits a neutrally charged solute transporter. Accordingly, in one embodiment, urea is used to prepare the hyperosmolar solution, and the concentration of urea in the hyperosmolar solution may be at any concentration between about 2.5-5.0 M or in certain other embodiments between about 3.1-6.0 M, between about 3.1-5.0 M, or between about 3.1-4.0 M. In another embodiment, the hyperosmolar solution comprises a urea analogue or a monosaccharide (e.g., glucose), which may be at a concentration of about 2.0-3.5 M, or between about 2.0-2.5 M, between about 2.5-3.0 M, or between 3.0-3.5 M, or between about 2.5-3.5 M. The concentration of urea, a urea analogue, a monosaccharide, or other neutrally charged small solute may be optimized by titration experiments so that an agent that inhibits the capability of an aquaporin to transport water is readily distinguished (i.e., quantifiably distinguishable) from the controls.

The hyperosmolar solution that contains the indicator cells (i.e., sample, suspension, or mixture) is then contacted with at least one candidate agent under conditions and for a time sufficient (as described herein) for the candidate agent to interact with (e.g., bind to) at least one aquaporin that is endogenously expressed or recombinantly expressed by the indicator cells. The indicator cells and the candidate agent are then removed from the hyperosmolar solution and combined with or diluted into a second solution (e.g., a physiological buffer, diluent, or media) that contains a reduced amount or totally lacks the solute of the hyperosmolar solution to obtain a substantially isosmolar solution, as described herein. After a period of time (as described above), the level of lysis of the indicator cells in the presence of the agent is determined and compared with the level of lysis of the indicator cells in the absence of the agent. In the absence of an aquaporin inhibitor (in either a control sample or a test sample containing an inactive agent), the influx of water into the indicator cells is rapid as the cell adapts to the change in the osmolar gradient. The rapid influx of water into the cells results in total or partial lysis of the indicator cells. An inhibitor of an aquaporin, thus protects the cell from lysis (i.e., inhibits, prevents, or decreases cell lysis). Therefore, the level of lysis of the indicator cells contacted with a candidate agent is less than the level of lysis of indicator cells that were not contacted with the candidate agent, thus indicating that the agent decreases or reduces the water permeability of the cell. For example, in a control sample that does not contain an agent or that contains an inactive agent, the percent of indicator cells lysed may be between 41%-100%, 50%-100%, 60%-100%, 70%-100%, 80%-100%, or 90%-100%. In a sample that contains an inhibitor of an aquaporin, the percent of indicator cells lysed may be between 0%-40%, 0%-30%, 0%-20%, 0%-15%, or 0%-10%.

Confirmatory Assays

Agents that alter transport of a neutrally charged, small solute or water by a solute transporter or an aquaporin, respectively, may be analyzed and further characterized by additional methods and techniques described herein and practiced in the art. Agents identified according to the methods described herein may be further characterized in dose-response experiments using the same cell lysis methods to determine the effective concentration of the agents. For example, an effective concentration of an inhibitor of a solute transporter ($EC_{50}$) may be calculated by non-linear regression to the equation: % lysis=% lysis$_{min}$+(% lysis$_{max}$·[inh]$^H$)/($EC_{50}^H$+[inh]$^H$), where [inh] is inhibitor concentration and H is the Hill coefficient.

To characterize particular agents, stopped-flow light scattering to measure solute and water permeabilities of a cell may be performed (see, e.g., Yang et al., *J Biol. Chem.* 277: 36782-86 (2002; Epub 2002 Jul. 19); Macey et al., *J. Membr. Biol.* 134(3):241-50 (1993)). For example, to determine urea permeability of a cell, dilutions of indicator cells, such as red blood cells, may be incubated with an agent and then subjected to an inwardly directed gradient of urea. After the cells osmotically shrink (i.e., the cell volume decreases), the kinetics of increasing cell volume caused by urea influx can be measured over a time course during which the cells are exposed to 90° scattered light intensity at 530 nm. As the volume of the cell increases, scattered light intensity is reduced.

Stopped flow light scattering may also be used to determine $EC_{50}$ values for inhibition by a solute transporter and may also be used to determine the sidedness of inhibitor action (i.e., whether the inhibitor alters a solute transporter activity by preventing or inhibiting entry of a solute into the cell or whether the inhibitor alters a solute transport activity by preventing or inhibiting efflux of the inhibitor from the cell).

Transporters

In certain embodiments, altering the volume of a cell comprises altering transport of a small, neutrally charged solute across a cell membrane by a transporter polypeptide. The methods described herein may be used for identifying agents that alter (i.e., increase or decrease in a statistically significant or biologically significant manner) the capability of a transporter polypeptide to transport a solute across a cell membrane. As described herein, transport of small, neutrally charged solutes and transport of water across a cell membrane can affect the volume of a cell. The methods described herein may be used to identify agents that inhibit or that promote the capability of a transporter to transport such a neutrally charged solute. Transporter polypeptides capable of transporting small, neutrally charged solutes include but are not limited to, urea transporter polypeptides, aquaporin polypeptides, and glucose transporter polypeptides.

The methods described herein may be used to identify agents that alter transport of a neutrally charged small molecule solute by a transporter expressed by animal cells. The animal may be a mammal, which may be a human, non-human primate, rodent (e.g., rat, mouse, hamster, rabbit), cow, goat, sheep, pig, camel, llama, cat, dog, or other mammal.

Urea Transporters

In certain embodiments, altering the volume of a cell comprises altering transport of urea across a cell membrane by a transporter polypeptide. Accordingly, in one embodiment, methods are provided for identifying potent inhibitors of urea transporters that can be used for treating diseases and conditions that result from, are associated with, or caused by aberrant urea transport in a cell. Previously, the only available UT inhibitors included compounds that were nonspecific and that exhibited moderate or low activity, such as the non-specific membrane intercalating agent phloretin (exhibiting activity at >0.5 mM); urea analogs such as thiourea, methylurea, and dimethylurea (exhibiting activity at 50-100 mM); (see, e.g., Mayrand et al., *J. Gen. Physiol.* 81:221-37 (1983); and chemically modified urea analogs (exhibiting irreversible activity at 30-100 µM) (Martial et al., *Pflügers Arch.* 423:51-58 (1993)).

Conservation of water in mammals depends significantly on the transport of urea, particularly in the kidney. Urea is generated as the major end product of hepatic nitrogen metabolism and is excreted primarily by the kidney. Urea and sodium chloride are the major solutes in the hyperosmolar renal medulla. In the antidiuretic kidney, urea is greatly concentrated with respect to plasma (up to 100 times in humans and 250 times in rodents) by countercurrent multiplication and exchange mechanisms (Bankir et al., *In The Kidney* (6th Edition), pages 637-679, Brenner, B M, ed., (WB Saunders Company, Philadelphia, Pa.) (2000)). Of central importance to these mechanisms is intrarenal urea recycling, which requires facilitated urea transport by molecular urea transporters (UTs). UTs are comprised of two major subfamilies encoded by different genes (UT-A and UT-B) (see, e.g., Bagnasco, *Am. J. Physiol.* 284:F3-F10 (2003); Shayakul et al., *Pflügers Arch.* 447:603-609 (2004); Yang et al., *J. Biol. Chem.* 273:9369-72 (1998)). In kidney, a single UT-B isoform is expressed in vasa recta while several splice variant UT-A-type transporters are expressed in kidney tubule epithelia (see, e.g., Sands, *Curr. Opin. Nephrol. Hypertens.* 13:525-32 (2004)). See also Karakashian et al., *J. Am. Soc. Nephrol.* 10: 230 37 (1999); Sands, *Mt Sinai J. Med.* 67:112 19 (2000); and Leroy et al., *Biochem. Biophys. Res. Commun.* 271:368-73 (2000)).

In one embodiment, methods are providing for identifying agents that alter (i.e., increase or decrease in a statistically significant or biologically significant manner) the capability of a urea transporter to transport urea across a cell membrane. In a particular embodiment, the methods described herein are useful for identifying agents that are inhibitors of a urea transporter, that is, agents that inhibit transport of urea across a cell membrane by at least one urea transporter. The methods may be used to identify agents that specifically interact with all urea transporters, to identify agents that specifically interact with only one subfamily of urea transporter (i.e., either UT-A transporters or UT-B transporters, and/or to identify agents that specifically interact with at least one but not all UT-A transporters.

As described herein, a urea transporter may be endogenously expressed by an indicator cell. Alternatively, an indicator cell comprises an exogenous polynucleotide (i.e., a polynucleotide that is introduced into a cell for recombinant expression of the transporter polypeptide) that encodes the urea transporter polypeptide and that directs expression of the transporter polypeptide in the indicator cell. The indicator cell may be transfected, transduced, or transformed with a recombinant expression vector that comprises such a polynucleotide according to molecular biology methods practiced in the art and described above. Exemplary nucleotide sequences that encode urea transporters, such as urea transporters in humans and rodents, are known in the art and are also readily available from public databases.

Five UT-A urea transporter isoforms (UT-A1, UT-A2, UT-A3, UT-A4, and UT-A5) are encoded by alternatively splicing of the Slc14A2 gene (see, e.g., Bagnasco et al., *Am. J. Physiol. Renal Physiol.* 281:F400-F406 (2001); Shayakul et al., *Pflugers Arch.* 447:603-609 (2004); Bagnasco, *Pflugers Arch.* 450:217-26 (2005); Sands, *Curr. Opin. Nephroi. Hypertens.* 13:525-32 (2004); Bagnasco, *Am. J. Physiol. Renal Physiol.* 284:F3-F10 (2003); Sands et al. *Am. J. Physiol.* 273:F321-39 (1997); Sands, *Annu. Rev. Physiol.* 65:543-66 (2003)). The Slc14A1 gene encodes a single UT-B isoform (see, e.g., Sands, *Curr. Opin. Nephroi. Hypertens.* 13:525-32 (2004); Lucien et al., *J. Biol. Chem.* 273:12973-80 (1998); Bagnasco, *Am. J. Physiol. Renal Physiol.* 284:F3-F10 (2003); Sidoux et al., *J. Biol. Chem.* 274:30228-35 (1999); see also e.g., Tsukaguchi et al., *J Clin Invest.* 99:1506-15 (1997)). Exemplary nucleotide sequences and the encoded polypeptide sequences may be found, for example, in GenBank Accession Nos. NM_007163.2 (UT-A); BC110445.1 (UT-A); BC110446.1 (UT-A); NM_007163.2(UT-A); AF349446.1 (UT-A1); X96969.1 (UT-A2); NM_015865.1 (UT-B); AY942197.1 (UT-B); BC050539.1 (UT-B); and Y19039.1 (UT-B).

Aquaporins

An opposing transport process to the transport of urea in cells is the transport of water. Water (a very polar molecule) may be transported through cell membranes, which comprise a lipid bilayer, by water channels composed of polypeptides known in the art as aquaporins. Aquaporins (AQPs) are a ubiquitous family of proteins characterized by sequence similarity and the presence of two tripeptide (Asp-Pro-Ala) motifs. The first transmembrane protein identified as a water transporter was cloned from mammalian red blood cells and was called CHIP28 for channel-forming integral protein of 28 kDal. Virtually all mammalian cells incorporate aquaporins into their cell membranes. Presently, at least twelve polypeptides that form water channels in human cells have been identified (see, e.g., Goodman, *Adv. Physiol. Educ.* 26:146-57 (2002); Magni et al., *Proteomics* 6:5637-49 (2006); Verkman, *Semin. Nephrol.* 26:200-208 (2006)). The human AQPs are divided into two subgroups according to their capability to transport only water molecules (e.g., AQP0, AQP1, AQP2, AQP4, AQP5, AQP6, and AQP8), or also transport glycerol and other small solutes (e.g., AQP3, AQP7, AQP9, AQP10, AQP12) (Magni et al., *Proteomics* 6:5637-49 (2006)).

Aquaporins have been identified in cells of the eye and blood-brain barrier, salivary glands, lungs, heart, spleen, pancreas, colon, red blood cells, and various parts of the nephron. Functions of aquaporins include facilitating water reabsorption in the kidney, assisting in maintaining fluid balance by facilitating rapid transepithelial transport, and minimizing the osmotic gradient and volume changes between cells and interstitium in the kidney (see, e.g., Ishibashi et al., *News Physiol. Sci.* 13:137-42 (1998); Verkman, *Water Channels*, Landis, Austin, Tex. (1993); Verkman, *Curr. Opin. Nephroi. Hypertens.* 9:517-22 (2000)). In addition, the amount of aquaporin polypeptides present in a cell and the capability of a cell to perform regulatory volume changes may be important for fluid secretions from exocrine glands.

By way of background, several aquaporins may be expressed in several cell types. For example, Aquaporin 0 is the major intrinsic protein (MIP) of lens fibre cells of the eye. The aquaporin initially called CHIP28 is now referred to aquaporin 1 in the art. Aquaporin (AQP1) is found in erythrocytes and is also found in the choroid plexus, the proximal tubule, and descending limb of the loop of Henle in the kidney. Aquaporin 2 (AQP2) (also called WCH-CD in the art) forms the water channel of the principal cell of the cortical and medullary collecting duct. Nephrogenic diabetes insipidus (NDI), the inability to produce concentrated urine, can result from several different malfunctions in the AQP2 system, which is controlled by anti-diuretic hormone (ADH). AQP3, AQP4, and AQP5 may be found in several tissues. In the kidney, AQP3 and AQP4 are located in the basolateral membrane of the renal cortical and medullary principal cell. AQP3 is also found in the gastrointestinal tract, and AQP4 is found in the brain.

In one embodiment, methods are providing for identifying agents that alter (i.e., increase or decrease in a statistically significant or biologically significant manner) the capability of an aquaporin to transport water across a cell membrane. In a particular embodiment, the methods described herein are useful for identifying agents that are inhibitors of a water transporter, that is, agents that inhibit transport of water by at least one aquaporin across a cell membrane. The methods may be used to identify agents that specifically interact with all aquaporins, to identify agents that specifically interact with only one subfamily of water transporters (i.e., either the aquaporins that transport water only or the aquaporins that are capable of transporting water and other molecules, such as glycerol). The methods may also be used to identify agents that specifically interact with at least one but not all aquaporins.

In particular embodiments, the methods described herein are useful for identifying agents that alter the transport of water by at least one of AQP0, AQP1, AQP2, AQP3, AQP4, AQP5, AQP6, AQP7, AQP8, AQP9, AQP10, AQP11, AQP12 (including AQP12A and AQP12A). In other embodiments, the methods described herein are useful for identifying agents that alter the transport of water by at least one of AQP1, AQP2, AQP3, and AQP4.

In a specific embodiment, the methods described herein are useful for identifying inhibitors of aquaporin polypeptides that transport both a solute such as glycerol and water (e.g., AQP3, AQP7, and AQP9). Indicator cells that comprise an aquaporin that transports glycerol and water and an aquaporin that transports only water (e.g., AQP0, AQP1, AQP2, AQP4, AQP5, AQP6, and AQP8). The indicator cells may be placed in a solution that comprises a neutrally charged solute (e.g., glycerol) in an amount sufficient to provide a hyperosmolar solution. After contacting the indicators cells in the hyperosmolar solution with at least one candidate agent, the hyperosmolar solution may be removed, replaced, or diluted such that the indicator cells are in a glycerol free (or solute free) medium that is substantially isosmolar. An increase in cell lysis compared to a similarly prepared sample in the absence of a candidate agent, indicates that the compound is an inhibitor of the solute-transporting aquaporin.

As described herein, an indicator cell may endogenously express an aquaporin. Alternatively, an indicator cell comprises an exogenous polynucleotide (i.e., a polynucleotide that is introduced into a cell for recombinant expression of the transporter polypeptide) that encodes an aquaporin polypeptide and that directs expression of the aquaporin transporter polypeptide in the indicator cell. The indicator cell may be transfected, transduced, or transformed with a recombinant expression vector that comprises such a polynucleotide according to molecular biology methods practiced in the art and described above. Numerous and exemplary polynucleotide sequences that encode aquaporin polypeptides, such as aquaporins in human cells and rodent cells, are known in the art and are available in publicly available databases, such as GenBank (see Internet web site at ncbi.nlm.nih.gov). By way of example, an SV40 immortalized rat submandibular acinar cell line has been transfected with a polynucleotide that encodes and directs expression of AQP5 (Hansen et al., *Pflügers Arch.* 5 Oct. 2006, Epub ahead of print).

Exemplary polynucleotide and the encoded polypeptide sequences may be found, for example, in GenBank Accession Nos. NM_198098.1 (AQP1); BC22486.1 (AQP1); AY953319.1 (AQP1); NM_000486.3 (AQP2); BC042496.1 (AQP2); Z29491.1 (AQP2); AF147092.1 (AQP2); NM_004925.3 (AQP3); NM_004028.3 (AQP4); U63623.1 (AQP4); U63622.1 (AQP4); BC045780.1 (AQP4); NM_001650.4 (AQP4); BC030745.1 (AQP4); NM_001651.1 (AQP5); BC034356.1 (AQP5); BC032946.1 (AQP5); BC065275.1 (AQP6); NM_001170.1 (AQP7); BC062701.1 (AQP7); NM_001169.2 (AQP8); BC040630.1 (AQP8); AF067797.1 (AQP8); NM_020980.2 (AQP9); AB008775.1 (AQP9); BC026258.1 (AQP9); BC069607.1 (AQP10); NM_080429.2 (AQP10); NM_173039.1 (AQP11); BC040443.1 (AQP11); NM_198998.1 (AQP12A); and BC041460.1 (AQP12B).

Monosaccharide Transporters

In another embodiment, methods described herein for identifying agents that alter the volume of a cell may be used for identifying agents that alter transport of a monosaccharide (e.g., glucose, fructose, galactose, ribose) across a cell membrane. In a particular embodiment, methods are provided for identifying agents that alter (i.e., decrease or increase in a statistically significant or biologically significant manner) the capability of a glucose transporter to transport glucose and/or other monosaccharides across a cell membrane.

Thirteen glucose transporters have been described. In certain embodiments, the methods described herein may identify agents that alter the capability of all members of the glucose transporter family to transport a monosaccharide (e.g., glucose, fructose, galactose) across a cell membrane. In more specific embodiments, methods described herein may be used to identify agents that alter the capability of at least one but not all the glucose transporters to transport a monosaccharide, such as glucose, across a cell membrane. Exemplary glucose transporters include, but are not limited to, transporter polypeptides called GLUT1, GLUT2, GLUT3, and GLUT4.

By way of background, GLUT 1 is expressed in many cell types. GLUT1 is one of the primary transporters across the blood brain barrier (Guo et al., *Biochem. Genet.* 43:175-87 (2005)). GLUT1 also transports glucose into astrocytes (Maurer et al., *FEBS Lett.* 580:4430-34 (2006); Epub 2006 Jul. 14)). The function of GLUT1 has also been studied with respect to its role in hypertension in diabetic nephropathy (see, e.g., Gnudi et al., *Curr. Hypertens. Rep.* 8:79-83 (2006)). Nephropathy is a major diabetic microvascular complication; both metabolic and hemodynamic perturbations influence its occurrence and progression toward end-stage renal disease.

The glucose transporter called GLUT3 transports glucose into neurons (Maurer et al., *FEBS Lett.* 580:4430-34 (2006); Epub 2006 Jul. 14)). GLUT2 is a facilitative glucose transporter located in a variety of cell types, including the plasma membrane of the liver, pancreatic, intestinal, kidney cells as well as in the portal and the hypothalamus areas. Due to its low affinity and high capacity, GLUT2 transports dietary sugars, glucose, fructose and galactose in a large range of physiological concentrations, and displays large bidirectional fluxes in and out the cells (Leturque et al., *J. Physiol. Biochem.* 61:529-37 (2005)). GLUT4 is the main glucose transporter activated by insulin in skeletal muscle cells and adipocytes (see, e.g., McGee et al., *Clin. Exp. Pharmacol. Physiol.* 33:395-99 (2006)). GLUT 7 is another transporter that also transports fructose (see, e.g., Manolescu et al., *J. Biol. Chem.* 280:42978-83 (2005)).

As described herein, an indicator cell may endogenously express a glucose transporter. Alternatively, an indicator cell may comprise an exogenous polynucleotide (i.e., a polynucleotide that is introduced into a cell for recombinant expression of the transporter polypeptide) that encodes a glucose transporter polypeptide and that directs expression of the glucose transporter polypeptide in the indicator cell. The indicator cell may be transfected, transduced, or transformed with a recombinant expression vector that comprises such a polynucleotide according to molecular biology methods practiced in the art and described above. Numerous and exemplary polynucleotide sequences that encode glucose transporter polypeptides, such as glucose transporters in human cells and rodent cells, are known in the art and are available in publicly available databases, such as GenBank (see Internet web site at ncbi.nlm.nih.gov). Exemplary polynucleotide and the encoded polypeptide sequences may be found, for example, in GenBank Accession Nos. NM_006516.1 (GLUT1); NM_000340.1 (GLUT2); BC060041.1 (GLUT2); L09674.1 (GLUT2); J03810.1 (GLUT2); NM_006931.1 (GLUT3); NM_001042.2 (GLUT4); NM 207420.1 (GLUT7); and NM_001001290.1 (GLUT9).

Indicator Cells

An indicator cell may be any cell, typically a eukaryotic cell, that comprises at least one aquaporin and/or at least one transporter that transports a small, neutrally charged solute (e.g., a urea transporter or a glucose transporter). The indicator cells may be used in suspension or the indicator cells may be attached to a substrate, such as a glass slide or a tissue culture dish, including multi-well plates (e.g., 96-well culture dishes). The substrate may be a solid impermeable surface, or the substrate may be a porous substrate that permits exposure of the apical and basolateral membranes of an indicator cell to a solution.

In certain embodiments, methods for identifying an agent that alters the capability of a solute transporter to transport a solute across a cell membrane may use indicator cells that endogenously express the transporter polypeptide. In other embodiments, the methods may use indicator cells that comprise an exogenous polynucleotide that encodes a solute transporter and directs the expression of the solute transporter. Similarly, methods for identifying an agent that alters the capability of an aquaporin to transport water across a cell membrane may use indicator cells that endogenously express at least one aquaporin or may use indicator cells that comprise an exogenous polynucleotide that encodes an aquaporin and directs the expression of the aquaporin. A cell that endogenously expresses a transporter has within the cell genome a nucleotide sequence that encodes a transporter and which nucleotide sequence is translated into mRNA, which is then transcribed.

In certain embodiments, methods for identifying an agent that alters transport of urea across a cell membrane may employ indicator cells that endogenously express a urea transporter polypeptide. An exemplary indicator cell that may be used in the methods described herein and that expresses a urea transporter is a red blood cell (i.e., erythrocyte), which endogenously expresses the urea transporter UT-B (also referred to as the Kidd blood group antigen). Red blood cells also express an aquaporin, AQP1.

Indicator cells may also include kidney cells (i.e., renal cells) that express at least one urea transporter and/or express at least one aquaporin. The kidney cells may be isolated from kidney tissue, established in cell culture by methods typically and routinely used in the art for establishing cell lines in culture, including methods for immortalizing cells. Other indicator cells include a neuron, brain cell, or a testis cell.

In another embodiment, indicator cells include cells that express and comprise in a cell membrane an aquaporin that transports glycerol as well as water (e.g., AQP3, AQP7, and AQP9) and that express and comprise in a cell membrane at least one aquaporin that transports only water (e.g., AQP0, AQP1, AQP2, AQP4, AQP5, AQP6, and AQP8). Compounds that inhibit transport of glycerol may be identified according to the methods described herein by using such indicator cells and by using glycerol as the solute in the hyperosmolar solution. Each aquaporin may be endogenously or exogenously expressed by the cell.

Indicator cells may be obtained or derived from a biological sample from any one of a number of animals, including mammals. Mammalian indicator cells may be obtained from humans; non-human primates; rodents such as mice, rats, or rabbits; cats (feline); dogs (canine); cattle (bovine); sheep (ovine); pigs (porcine); llamas; and camels, for example.

A biological sample as used herein refers in certain embodiments to a sample containing at least one indicator cell or a plurality of indicator cells. A biological sample may be a blood sample, such as whole blood or a cellular fraction of whole blood, biopsy specimen, body fluids that contain cells that express at least one transporter (e.g., lung lavage, ascites, mucosal washings, synovial fluid), bone marrow, lymph nodes, tissue explant, organ culture, or any other tissue or cell preparation from a subject or a biological source. A biological sample may further refer to a tissue or cell preparation in which the morphological integrity or physical state of the tissue has been disrupted, for example, by dissection, dissociation, solubilization, fractionation, homogenization, biochemical or chemical extraction. The subject or biological source may be a human or non-human animal, a primary cell culture (e.g., kidney cells or other cells that endogenously express a transporter), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

Indicator cells, including kidney cells or cells derived from other tissues, may comprise an exogenous polynucleotide that encodes a solute transporter polypeptide or an aquaporin. The indicator cell may be transfected, transformed, or transduced with a recombinant expression vector, which comprises a polynucleotide that is capable of directing expression of at least one solute transporter or at least one aquaporin. To direct expression of at least one transporter, the polynucleotide comprises a nucleotide sequence that encodes a transporter such as an aquaporin, a urea transporter, a glucose transporter, or a transporter that transports another small neutrally charged solute, which nucleotide sequence is operatively linked to at least one expression control sequence (e.g., a promoter, enhancer, transcriptional control element, and the like). Recombinant expression vectors may be prepared according to methods and techniques with which a person skilled in the molecular biology art is familiar and which are described herein. An exemplary cell line that may be transfected with a recombinant expression vector comprising a polynucleotide that directs expression of a urea transporter or other transporter or aquaporin includes Madin-Darby canine kidney cells (MDCK).

Indicator cells containing the described recombinant expression constructs may be genetically engineered (transduced, transformed, or transfected) with vectors and/or expression constructs (for example, a cloning vector, a shuttle vector, or an expression construct). The vector or construct may be in the form of a plasmid, a viral particle, a phage, etc. The engineered indicator cells can be cultured in conventional nutrient media modified as appropriate for activating promoters, selecting transformants, or amplifying particular genes or encoding-nucleotide sequences. Selection and maintenance of culture conditions for particular indicator cells, such as temperature, pH and the like, will be readily apparent to the ordinarily skilled artisan. Preferably the indicator cell can be adapted to sustained propagation in culture to yield a cell line according to art-established methodologies. In certain embodiments, the cell line is an immortal cell line, which refers to a cell line that can be repeatedly passaged in culture (at least ten times while remaining viable) following log-phase growth. In other embodiments the indicator cell used to generate a cell line that is capable of unregulated growth, such as a cancer cell, or a transformed cell, or a malignant cell.

Useful recombinant expression constructs are prepared by inserting into an expression vector a structural DNA sequence encoding the transporter polypeptide together with suitable translation initiation and termination signals in operable reading phase with a functional promoter. The construct may comprise one or more phenotypic selectable markers and an origin of replication to ensure maintenance of the vector construct and, if desirable, to provide amplification within the indicator cell. A particular plasmid or vector may be used as long as it is replicable and viable in the indicator cell. Thus, for example, the polynucleotides that encode a transporter polypeptide may be included in any one of a variety of expression vector constructs for expressing a polypeptide.

An appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual*, 3rd Ed., (Cold Spring Harbor Laboratory 2001)); Maniatis et al. (*Molecular Cloning*, (Cold Spring Harbor Laboratory 1982)), and elsewhere.

The nucleotide sequence encoding a transporter polypeptide in the expression vector is operatively linked to at least one appropriate expression control sequence (e.g., a promoter or a regulated promoter) to direct mRNA synthesis. Representative examples of such expression control sequences include LTR or SV40 promoter, the *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a polynucleotide described herein is well within the level of ordinary skill in the art.

The vector may be a viral vector such as a retroviral vector. For example, retroviruses from which the retroviral plasmid vectors may be derived include, but are not limited to, Moloney Murine Leukemia Virus, spleen necrosis virus, Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. A viral vector also includes one or more promoters. Suitable promoters that may be employed include, but are not limited to, the retroviral LTR; the SV40 promoter; and the human cytomegalovirus (CMV) promoter described in Miller et al., *Biotechniques* 7:980-990 (1989), or any other promoter (e.g., eukaryotic cellular promoters including, for example, the histone, pol III, and β-actin promoters). Other viral promoters that may be employed include, but are not limited to, adenovirus promoters, thymidine kinase (TK) promoters, and B19 parvovirus promoters.

The retroviral plasmid vector is employed to transduce packaging cell lines (e.g., PE501, PA317, ψ-2, ψ-AM, PA12, T19-14X, VT-19-17-H2, ψCRE, ψCRIP, GP+E-86, GP+en-vAm12, DAN; see also, e.g., Miller, *Human Gene Therapy*, 1:5-14 (1990)) to form producer cell lines. The vector may transduce the packaging cells through any means known in the art, such as, for example, electroporation, the use of liposomes, and calcium phosphate precipitation. The producer cell line generates infectious retroviral vector particles that include the nucleic acid sequence(s) encoding the polypeptides or fusion proteins described herein. Such retroviral vector particles then may be employed, to transduce eukaryotic cells. Eukaryotic cells that may be transduced include, for example, embryonic stem cells, embryonic carcinoma cells, hematopoietic stem cells, hepatocytes, fibroblasts, myoblasts, keratinocytes, endothelial cells, bronchial epithelial cells, and other culture-adapted cell lines.

Agents

Agents (which may also be referred to as bioactive agents) may be provided as "libraries" or collections of compounds, compositions, or molecules. For example, agents include low molecular weight, organic molecules, which typically include compounds known in the art as "small molecules." A small molecule may have a molecular weight less than $10^5$ daltons, less than $10^4$ daltons, or less than $10^3$ daltons. Other agents that may be useful for altering the volume of a cell (e.g., an agent that alters the capability of a transporter to transport a solute across a cell membrane or an agent that alters the capability of an aquaporin to transport water across a cell membrane) include peptides. Peptides and small molecules may be synthesized according to methods routinely practiced by person skilled in the synthesis of peptides or small molecules, respectively.

The methods described herein are useful for screening large numbers of agents (e.g., multiple hundreds of agents) quickly. Candidate agents, such as small molecules and peptides, may be obtained from combinatorial libraries. Combinatorial libraries of agents can be purchased from a commercial vendor or can be prepared according to methods with which a skilled artisan is familiar. Examples of methods for the synthesis of molecular libraries can be found in the art, for example in DeWitt et al., *Proc. Natl. Acad. Sci. U.S.A.* 90:6909 (1993); Erb et al., *Proc. Natl. Acad. Sci. USA* 91:11422 (1994); Zuckermann et al., *J. Med. Chem.* 37:2678 (1994); Cho et al., *Science* 261:1303 (1993); Carrell et al., *Angew. Chem. Int. Ed. Engl.* 33:2059 (1994); Carell et al., *Angew. Chem. Int. Ed. Engl.* 33:2061 (1994); and in Gallop et al., *J. Med. Chem.* 37:1233 (1994).

Candidate agents that are provided as members of a combinatorial library, include synthetic agents prepared according to a plurality of predetermined chemical reactions performed in a plurality of reaction vessels. For example, various starting compounds may be prepared according to one or more of solid-phase synthesis, recorded random mix methodologies, and recorded reaction split techniques that permit a given constituent to traceably undergo a plurality of permutations and/or combinations of reaction conditions. The resulting products comprise a library that can be screened followed by iterative selection and synthesis procedures. Such synthetic combinatorial libraries include a library of peptides (see, e.g., International Patent Application Nos. PCT/US91/08694 and PCT/US91/04666) or other compositions that may include small molecules as provided herein (see, e.g., International Patent Application No. PCT/US94/08542, EP Patent No. 0774464, U.S. Pat. No. 5,798,035, U.S. Pat. No. 5,789,172, U.S. Pat. No. 5,751,629, which are hereby incorporated by reference in their entireties).

Agents identified by the methods described herein include agents that are capable of inhibiting transport of urea across a cell membrane, and inhibiting entry of urea into a cell and/or inhibiting efflux of urea out of the cell. Provided herein are compounds that are potent urea transporter inhibitors, which include inhibitors of UT-B, which were identified using the methods described herein. The exemplary compounds belong to four diverse chemical classes including but not limited to phenylsulfoxyoxazoles and phenylsulfoxyimidazoles, benzenesulfonanilides, phthalazinamines, and aminobenzimidizoles, which had submicromolar $EC_{50}$ values in red blood cell lysis assays and in stopped flow light scattering assays.

Agents and compounds identified and characterized by the methods described herein may be used in pharmaceutical compositions for treating diseases, disorders, and conditions related to aberrant solute or water transport. For example, an inhibitor of an aquaporin may be used to increase renal water clearance in hyponatremia associated with fluid overload or SIADH (Goldsmith, *Am. J. Cardiol.* 95:14 B-23B (2005); Miller, *J. Am. Geriatr. Soc.* 54:345-53 (2006)). An agent identified by the methods described herein, which may be an inhibitor of a urea transporter, may be used to treat or ameliorate conditions, disorders, and diseases related to aberrant urea transport such as conditions related to aberrant renal urea clearance. Such diseases, disorders, and conditions include cardiovascular disease (e.g., hypertension and congestive heart failure), syndrome of inappropriate antidiuretic hormone secretion (SIADH), cirrhosis, azotemia, acute renal failure, chronic renal insufficiency, fluid retention, and abnormal uresis. An agent identified by the methods described herein, which may be an inhibitor of a glucose transporter, may be used to treat or ameliorate conditions, disorders, and diseases related, in part, to aberrant glucose transport, such as diabetes.

The agents identified according to the methods described herein, for example, agents that are urea transporter inhibitors may be used for developing animal models that mimic a urea transporter knock-out animal model. For example, by administering a UT-B inhibitor to an animal, thus creating a "UT-B chemical knock out" animal, the mechanism and activities of other urea transporters may be studied and analyzed. Similarly, chemical UT-A knock out animals may be made by administering an inhibitor of a UT-A transporter, or by administering an inhibitor specific for one UT-A isoform. Such models would also be useful for determining the specificity and selectivity of a urea transporter inhibitor (see, e.g., Klein et al., *J. Am. Soc. Nephrol.* 15:1161-67 (2004)).

Treatment of Diseases and Disorders Related to Fluid Retention Imbalance

A composition comprising an agent that inhibits transport of a neutrally charged solute transport (e.g., urea) by a solute transporter and/or that inhibits transport of water by an aquaporin may be used for treating a disease, disorder, or condition in a subject. Diseases, disorders, and conditions that may be treated with compounds that inhibit solute transport or water transport, including those compounds described herein, include cardiovascular diseases (such as hypertension or congestive heart failure), syndrome of inappropriate antidiuretic hormone secretion (SIADH), cirrhosis, azotemia, acute renal failure, chronic renal insufficiency, fluid retention, diabetes, and abnormal uresis. In one embodiment, compounds that inhibit urea transporters (i.e., that inhibit transport of urea across a cell membrane, including across the outer cell membrane into (influx) or out of the cell (efflux)) may be used as a type of diuretic, a "urearetic," that affects renal urea clearance mechanisms.

Methods are also provided for using the compounds identified by the methods described herein for treating a disease, disorder, or condition associated with or related to aberrant transport of a neutrally charged solute (e.g., urea, a monosaccharide, such as glucose) in a subject by administering to the subject in need thereof a pharmaceutical composition comprising at least one compound that is a specific inhibitor of a transporter capable of transporting the solute across a cell membrane. In another embodiment, methods are provided for treating a disease, disorder, or condition that is associated with or related to aberrant transport of water by an aquaporin.

A disease, disorder, or condition that is related to aberrant urea transporter activity includes a disease, disorder, or condition that is caused by, in whole or in part, by aberrant urea transport and also includes a disease, disorder, or condition for which aberrant urea transporter activity is a sequelae of the disease, disorder, or condition. The disease, disorder, or condition that may be treated using a compound that inhibits urea transporter activity may be associated with a fluid retention imbalance such as urea clearance insufficiency. Urea is a by-product of protein metabolism that is formed in the liver. Because urea contains ammonia, which is toxic to an animal body, urea must be quickly filtered from the blood by the kidneys and excreted in the urine. Also as described herein, conservation of water in mammals depends significantly on the transport of urea, particularly in the kidney. Urea is generated as the major end product of hepatic nitrogen metabolism and is excreted primarily by the kidney. In a particular embodiment, the disease, disorder, or condition associated with aberrant urea transport is renal urea clearance insufficiency.

In one embodiment, treating any one of the aforementioned diseases, disorders, or conditions comprises inhibiting (i.e., preventing, decreasing, reducing, abrogating, or inhibiting in a statistically significant or biologically significant manner) the capability of at least one urea transporter to transport urea by administering a composition comprising a compound that specifically interacts with a urea transporter resulting in inhibition, loss, or prevention of urea transport. The compound may inhibit a UT-B transporter and/or may inhibit at least one UT-A transporter or isoform thereof (e.g., UT-A1, UT-A2, UT-A3, UT-A4, UT-A5).

To evaluate and to monitor the effectiveness of a compound to treat a disease, disorder, or condition, one or more of several clinical assay methods may be performed that are familiar to a person skilled in the clinical art. For example, a clinical method called a urea clearance test may be performed. A blood sample is obtained from a subject to whom the compound is being administered so that the amount of urea in the bloodstream can be determined. In addition, a first urine sample is collected from the subject and at least one hour later, a second urine sample is collected. The amount of urea quantified in the urine indicates the amount of urea that is filtered, or cleared by the kidneys into the urine. Another clinical assay method measures urine osmolality (i.e., the amount of dissolved solute particles in the urine). Inability of the kidneys to concentrate the urine in response to restricted fluid intake, or to dilute the urine in response to increased fluid intake during osmolality testing may indicate decreased kidney function.

Urea is a by-product of protein metabolism and is formed in the liver. Urea is then filtered from the blood and excreted in the urine by the kidneys. The BUN (blood urea nitrogen) test measures the amount of nitrogen contained in the urea. High BUN levels may indicate kidney dysfunction, but because blood urea nitrogen is also affected by protein intake and liver function, the test is usually performed in conjunction with determination of blood creatinine, which is considered a more specific indicator of kidney function. Low clearance values for creatinine and urea indicate diminished ability of the kidneys to filter these waste products from the blood and excrete them in the urine. As clearance levels decrease, blood levels of creatinine and urea nitrogen increase. An abnormally elevated blood creatinine, a more specific and sensitive indicator of kidney disease than the BUN, is diagnostic of impaired kidney function.

As used herein, a subject may be any mammal, including a human, that may have or be afflicted with a disease, condition, or disorder described herein. A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising a compound that inhibits transport of a neutrally charged solute by a transporter may be formulated for sustained or slow release. Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

The dose of the composition for treating a disease or disorder associated with a fluid retention imbalance such as urea clearance insufficiency or for treating cardiovascular diseases (such as hypertension or congestive heart failure), syndrome of inappropriate antidiuretic hormone secretion (SIADH), cirrhosis, azotemia, acute renal failure, chronic renal insufficiency, fluid retention, diabetes, and abnormal uresis may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

Pharmaceutical compositions may be administered in a manner appropriate to the disease to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity).

Optimal doses may generally be determined using experimental models and/or clinical trials. The optimal dose may depend upon the body mass, weight, or blood volume of the subject. In general, the amount of a small molecule compound as described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein.

The following Examples are offered for the purpose of illustrating the present invention and are not to be construed to limit the scope of this invention.

EXAMPLES

Example 1

Red Blood Cell (RBC) Lysis Assay

An RBC lysis assay was developed in an automated, 96-well format high throughput format and optimized for identification and characterization of small-molecule UT-B inhibitors. Inhibition of UT-B mediated transport of urea by compounds was indicated by increased RBC lysis when urea- or acetamide-loaded RBCs were rapidly diluted into PBS (see FIG. 1). Conditions were optimized to give a robust assay for high-throughput screening that exhibited high sensitivity and a low false-positive rate. Absorbance at 710 nm was measured as a read-out of RBC lysis to minimize interference by test compounds and hemoglobin.

Screening of compounds for UT-B inhibitory activity in the RBC lysis assay was performed using a BECKMAN COULTER (Fullerton, Calif.) integrated system that included a 3-meter robotic arm, microplate carousel, liquid handling work station with parallel 96-well solution mixing and transfer (BIOMEK FX), plate sealer, and two fluorescence plate readers (FLUOstar Optima; BMG LABTECH Gmbh; Durham, N.C.), each equipped with a 710±5 nm absorption filter (CHROMA, Rockingham, Vt.). Chemicals were purchased from SIGMA-ALDRICH (St. Louis, Mo.) unless otherwise noted.

Mouse and Human Blood Collection

Human venous blood obtained from a single donor was collected into VACUTAINERS coated with sodium heparin (BECTON-DICKINSON, Franklin Lakes, N.J.), stored at 4° C., and used within 48 hr of collection. All human procedures were approved by the University of California, San Francisco Committee on Human Research. Whole mouse blood was collected from 8-12 week-old (25-35 g) wild-type; AQP1-null (Ma et al., *J. Biol. Chem.* 273:4296-99 (1998)); or UT-B-null (Yang et al., *J. Biol. Chem.* 277:10633-37 (2002)) mice in a CD1 genetic background by orbital puncture following subcutaneous injection with sodium heparin (150 USP units). All animal protocols were approved by the University of California, San Francisco Committee on Animal Research.

Assay Development

Inhibition of UT-B mediated transport of urea by compounds was indicated by increased RBC lysis when urea- or acetamide-loaded RBCs were rapidly diluted into PBS (see FIG. 1). Conditions were optimized to give a robust assay for high-throughput screening that exhibited high sensitivity and a low false-positive rate. Absorbance at 710 nm was measured as a read-out of RBC lysis to minimize interference by test compounds and hemoglobin. Urea and a panel of small urea-like solutes (e.g., formamide, N-methylurea, acetamide, propionamide, butyramide, and isobutyramide) were evaluated as the loading solute based on their transport kinetics and passage through UT-B. Acetamide was selected because its equilibration in RBCs was approximately 2-fold slower than water, which is optimal in an osmotic lysis assay, and because greater than 95% of its transport in RBCs is UT-B-dependent as determined by stopped-flow light scattering.

Figure 2:
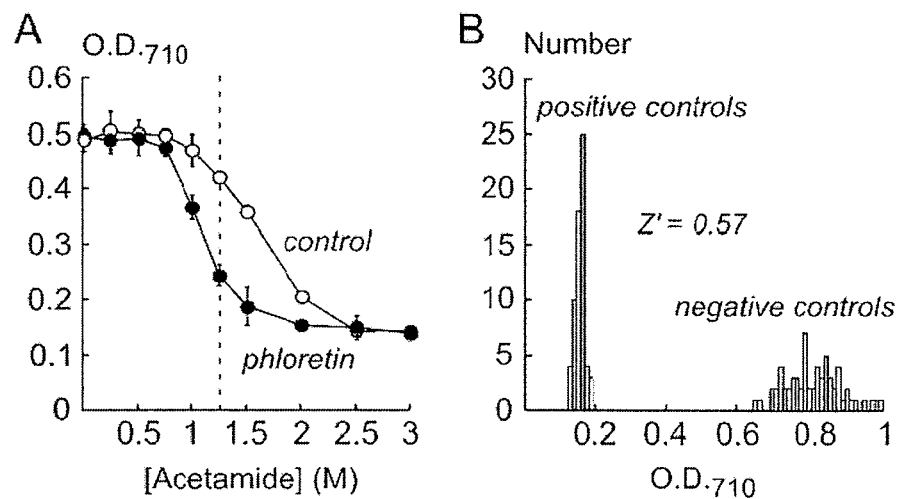
FIG. 2(A-B) presents graphs illustrating the red blood cell lysis assay.

The acetamide loading concentration that is optimal for identifying UT-B inhibitors was determined. FIG. 2A shows RBC lysis, determined by absorbance at 710 nm ($O.D._{710}$), as a function of the acetamide concentration used to load RBCs prior to mixing with acetamide-free buffer. Greater lysis, which is indicated by reduced $O.D._{710}$, was observed with increasing acetamide concentration. Fifty percent lysis was observed at approximately 1.6 M acetamide under control conditions (open circles) and at approximately 1.1 M when UT-B-facilitated acetamide transport was inhibited by phloretin (filled circles). To distinguish between control vs. inhibited UT-B, a concentration of 1.25 M acetamide (dashed vertical line) was chosen for the assay. Other technical considerations that were addressed during assay optimization included maintenance of RBC viability and uniform suspension, mixing conditions (rates, volumes and pipette tip locations in wells) and incubation time/temperature. The goodness of the optimized assay was evaluated by screening a series of plates containing positive and negative controls (100% and 0% lysis, respectively), which gave a very good statistical z'-factor of 0.57 for the screen (see FIG. 2B).

Example 2

High Throughput Screening of Small Molecule Libraries for UT-B Inhibitors

A primary screening for UT-B inhibitors was performed using a collection of 50,000 diverse, drug-like compounds (>90% with molecular size of 250-500 Da) obtained from a commercial source (CHEMDIV Inc., San Diego, Calif.). 96-well plates containing four compounds per well (each at 2.5 mM) were prepared for screening and then stored frozen in DMSO until use. Plates containing one compound per well (at 10 mM in DMSO) were stored separately and used later to identify and characterize individual active compounds.

Whole human blood was collected (see Example 1) and then prior to performance of the assay was diluted to a hematocrit of 1% in hyperosmolar PBS containing 1.25 M acetamide and 5 mM glucose (1550 mOsm, measured using freezing point-depression osmometry; Precision Systems, Natick, Mass.). Identical assay results were obtained when washed/centrifuged RBCs were used instead of whole blood. RBC suspensions were maintained at room temperature for up to 2 hr by periodic pipette mixing. Ninety-nine μL from a reservoir containing the RBC suspension was added to each well of a 96-well round-bottom microplate (FALCON, BECTON DICKINSON), to which test compounds were added (1 μL, 25 μM final compound concentration, 1% final DMSO concentration). After 6 min incubation, 20 μL of the RBC suspension was added rapidly to each well of a 96-well black-walled plate (COSTAR, Corning, N.Y.) containing 180 μL isosmolar buffer (PBS containing 1% DMSO) in each well. Vigorous mixing was achieved by repeated pipetting.

RBC lysis was quantified from a single time-point measurement of absorbance at 710-nm wavelength (Mazeron et al., *Photochem. Photobiol.* 72:172-78 (2000); Cohn et al., *Mol. Biochem. Parasitol.* 132:27-34 (2003)) made within 5 min after hyposmolar shock. Absorbance values were stable for at least 1 hr. Each assay plate contained eight negative 'no-lysis' controls (isotonic buffer; PBS+1.25 M acetamide with 1% DMSO) and eight positive 'full-lysis' controls (distilled $H_2O$ with 1% DMSO) that were mixed with DMSO vehicle-treated blood.

The statistical z'-factor, indicating 'goodness of the assay,' (Oldenburg et al., eds. *Handbook of Drug Screening*, New York, N.Y.; Marcel Dekkar, Inc. 549-554 (2001)) was computed using data from test plates as defined by: $z'=1-3[(SD_{pos}+SD_{neg})/(A_{pos}-A_{neg})]$, where $SD_i$ and $A_i$ are the standard deviations and mean absorbance values for positive (pos) and negative (neg) controls. The percentage of RBC lysis in each test well of a given plate was calculated using control values from the same plate as follows: % lysis=100%·$(A_{neg}-A_{test})/(A_{neg}-A_{pos})$, where $A_{test}$ is the absorbance value from a test well. During assay optimization, some test wells were incubated with the non-specific UT-B inhibitor phloretin (0.7 mM, dissolved at 100× in DMSO stock solution) as an additional positive control.

Figure 3:
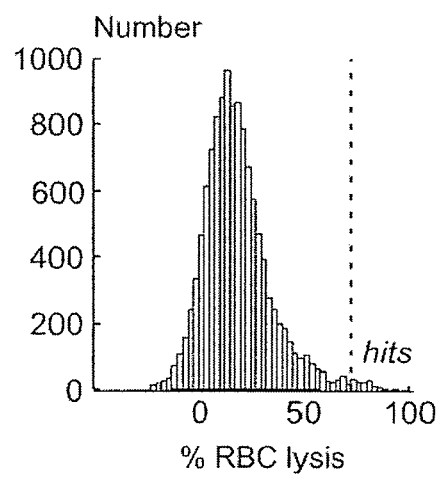
FIG. 3 presents a frequency histogram of percent erythrocyte lysis for a primary screen (12,500 test wells with 4 compounds per well; 50,000 compounds total). The dashed line representing the percent RBC lysis chosen to define 'hits.'

FIG. 3 shows the frequency histogram of $O.D._{710}$ values for all test compounds in the primary screen. Most compounds showed no significant apparent UT-B inhibition based on little (<30%) RBC lysis. Approximately 100 compounds producing greater than 75% lysis were selected for further evaluation.

Example 3

Stopped Flow Light Scattering Confirmatory Assay for Identification of UT-B Inhibitors RBC urea and water permeabilities were assayed by stopped-flow light scattering using a Hi-Tech Sf-51 instrument (Wiltshire, UK). For measurement of urea permeability, dilutions of whole blood (human or mouse; see Example 1) in PBS (hematocrit: approximately 0.5%) were incubated with test compounds for 5 min and then subjected to a 250-mM inwardly directed gradient of urea. After an initial osmotic shrinking phase, the kinetics of increasing cell volume caused by urea influx were measured as the time-course of 90° scattered light intensity at 530 nm, with increasing cell volume resulting in reduced scattered light intensity. As a positive control, 0.7 mM phloretin was added to the RBC suspension prior to stopped-flow experiments. Measurements of water permeability were carried out similarly, with sucrose (cell-impermeant) used instead of urea to establish a 250-mM osmotic gradient. As a positive control, $HgCl_2$ (0.3 mM) was added to the RBC suspension prior to stopped-flow measurements. Osmotic water permeability coefficients ($P_f$) were computed from light scattering data as described (van Hoek et al., *J. Biol. Chem.* 267:18267-69 (1992)).

After repeating the 96-well plate RBC lysis assay to confirm compound activity (see Example 2), bona fide urea transport inhibition was determined by stopped-flow light scattering from the kinetics of urea influx (RBC swelling) in response to an inwardly directed urea gradient. Rapid mixing of an RBC suspension with a hyperosmolar solution containing excess 250 mM urea produced rapid cell shrinking due to osmotic water efflux, followed by cell swelling as urea (and water) influx occurred.

Figure 4:
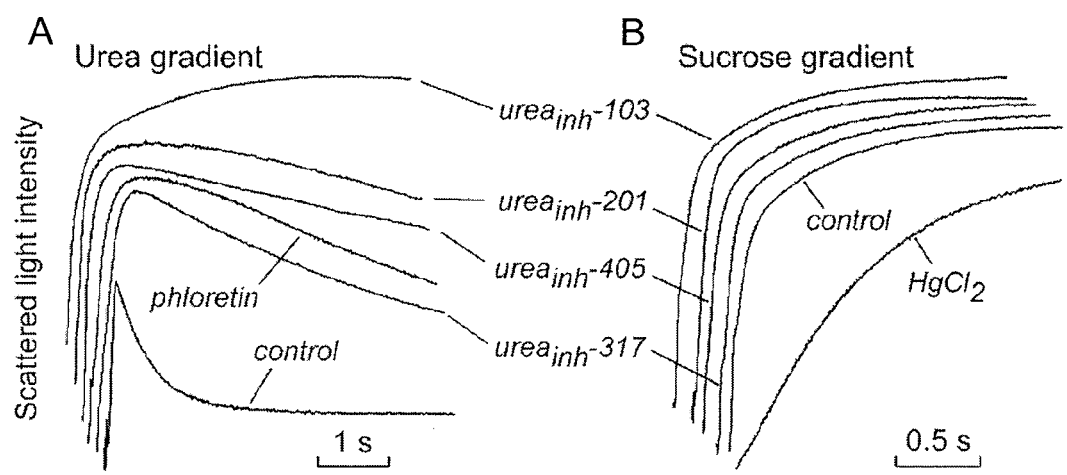
FIGS. 4A-B illustrate urea permeability measured by light scattering. (A) Urea permeability was measured from the kinetics of light scattering in response to a 250-mM inwardly directed urea gradient in the absence of inhibitor (control) or in the presence of 0.7 mM phloretin (positive control) or 5 µM of indicated compounds. (B) Osmotic water permeability of human RBCs was measured by light scattering in response to a 250-mM inwardly directed sucrose gradient in the absence or presence of 0.3 mM $HgCl_2$ (positive control) or 25 µM of each inhibitor.

Thirty-two compounds in four distinct chemical structural classes (phenylsulfoxyoxazole, benzenesulfonanilide, phthalazinamine, and aminobenzimidazole) were identified that at 5 µM produced substantial inhibition (greater than 95%) of UT-B-facilitated urea transport. Other compounds, that exhibited either much lower or no activity in the stopped-flow assay, probably had apparent UT-B inhibitory activity in the primary screen in part due to RBC toxicity and consequent increased lysis. Original stopped-flow urea transport data for one representative compound (at 5 µM) of each class is shown in FIG. 4A. Tracings from control (no inhibitors) and phloretin-treated RBCs are provided for comparison. The new compounds at 5 µM inhibited UT-B-facilitated urea transport in human RBCs by greater than 95%, which was as good as or better than that with 0.7 mM phloretin. FIG. 4B shows that none of the UT-B inhibitors when tested at an even higher concentration of 25 µM, inhibited RBC osmotic water permeability as measured by cell shrinking in response to a sucrose gradient. Curves from negative control (no inhibitor) and positive control ($HgCl_2$ water transport inhibitor) are provided for comparison.

Example 4

Structure Activity Relationship Studies of UT-B Inhibitors

The activity of approximately 700 commercially available analogs (CHEMDIV Inc. and Asinex; Moscow, Russia) of active compounds from the four distinct chemical structural classes (phenylsulfoxyoxazole (also phenylsulfoxyimidazole, phenylsulfoxythiazole), benzenesulfonanilide, phthalazinamine, and aminobenzimidazole) identified in the primary screen was determined to establish structure-activity relationships (SAR) and, potentially, to identify compounds with improved UT-B inhibitory potency. These compounds were tested against human and mouse UT-B using the RBC lysis assay. For some of the more active compounds, dose-response experiments were performed using human and/or mouse blood in the lysis assay. $EC_{50}$ was calculated by non-linear regression to the equation: % lysis=% $lysis_{min}$+(% $lysis_{max}$·$[inh]^H$)/($EC_{50}^H$+$[inh]^H$), where [inh] is inhibitor concentration and H is the Hill coefficient.

Figure 5:
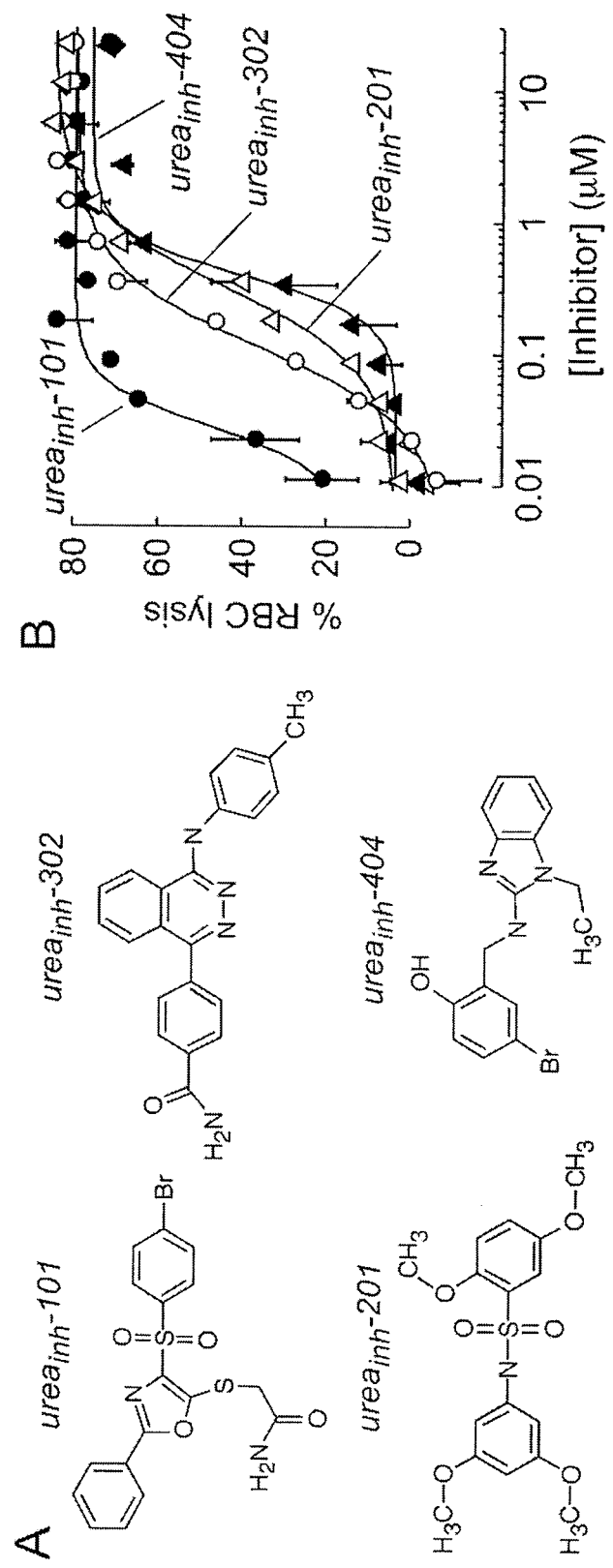
FIG. 5A presents the chemical structures of representative UT-B inhibitors ($urea_{inh}$), identified from primary high-throughput screening and assay of analogs.
FIG. 5B presents dose-inhibition data for the inhibitors shown in FIG. 5A determined by the lysis assay using human RBCs (±SD) and fit to calculate $EC_{50}$ (solid lines) as described in Example 4.

The analogs were screened at 25 µM. Concentration-inhibition data were obtained for those compounds producing greater than 75% apparent UT-B inhibition by the RBC lysis assay. FIG. 5A shows the chemical structures of potent compounds from each of the phenylsulfoxyoxazole, benzenesulfonanilide, phthalazinamine, and aminobenzimidazole classes. These structures are unrelated to either phloretin or urea analog inhibitors. FIG. 5B shows concentration-inhibition data with apparent $EC_{50}$ values (in nM) for exemplary compounds: $urea_{inh}$-101, 30 nM; $urea_{inh}$-201, 300 nM; $urea_{inh}$-302, 100 nM; and $urea_{inh}$-404, 400 nM.

Example 5

Determination of $EC_{50}$ of Urea Transport Inhibitors

To determine $EC_{50}$ values for urea transport inhibition directly, RBC urea transport was measured by stopped-flow light scattering using a non-saturating concentration of extracellular urea (to avoid possible competition effects). $EC_{50}$ for inhibition of RBC urea transport was determined independently by comparing stopped-flow light scattering curves to a model of cell shrinking-swelling.

For stopped-flow experiments, a 100-mM gradient of urea (for human RBCs) or N-methylurea (for mouse RBCs) was used to minimize competition effects (apparent urea and N-methylurea affinities at 23° C. are approximately 200 and approximately 100 mM, respectively) (Mayrand et al., *J. Gen. Physiol.* 81:221-37 (1983)). N-methylurea, with greater than 2-fold slower RBC permeability than urea, was used in mouse studies to better resolve overlapping water and urea transport kinetics. Dose-response data were also collected for human RBCs using a high concentration of 1 M urea to distinguish between competitive vs. non-competitive inhibitor binding.

The two coupled differential equations describing water efflux and solute influx in response to externally added urea or methylurea were numerically integrated using the forward Euler method (Δt=0.01 s) to reproduce the biphasic changes in cell volume observed experimentally. Computations that were performed using the smaller time step (Δt=0.001 s) gave similar results, confirming the adequacy of the 0.01 s time step. Water flux, $J_v$ (in $cm^3$/s), across erythrocyte membranes is represented by the following equation: $J_v$=−$P_f$·S·$v_w$·[($I_e$−$I_c$(i))+($U_e$−$U_c$(i))]; solute flux, $J_s$ (in mol/s), is represented by the following equation: $P_s$·S·($U_e$−$U_c$(i). Permeability coefficients ($P_f$ and $P_s$) are expressed in units of cm/s, cell surface area (S) in $cm^2$, extracellular (e) and cellular (c) concentrations of impermeant (I) and urea/methylurea (U) solute in mol/$cm^3$, and $v_w$ is 18 mol/$cm^3$. Initial conditions were $I_e$=$I_c$(0)=2.9×$10^{-4}$ mol/$cm^3$, $U_e$=$10^{-4}$ mol/$cm^3$, and $U_c$(0)=0. For each time step, a new cell volume (normalized to the initial size; V(i+1)/V(0)) and a new cell permeant concentration (U(i+1)) were calculated from V(i+1)/V(0)=V(i)/V(0)−Δt·$P_f$·(S/V(0))·$v_w$·[$I_e$(1−V(i)/V(0))+($U_e$−$U_c$(i))] and $U_c$(i+1)=$U_c$(i)/V(0)−Δt·$U_s$·(S/V(0))·$v_w$·($U_e$−$U_c$(i)). Normalized cell volume was assumed to be inversely proportional to scattered light intensity. The product of $P_f$ and the surface area-to-volume ratio (S/V(0)) was determined to be 3.4×$10^2$ $s^{-1}$ and 8.5×$10^2$ $s^{-1}$ for human and mouse erythrocytes, respectively, from water permeability measurements. $P_s$ was varied to reproduce experimental data, and $EC_{50}$ was computed using non-linear regression (see above) of $P_s$ vs. [inh] data.

Figure 6:
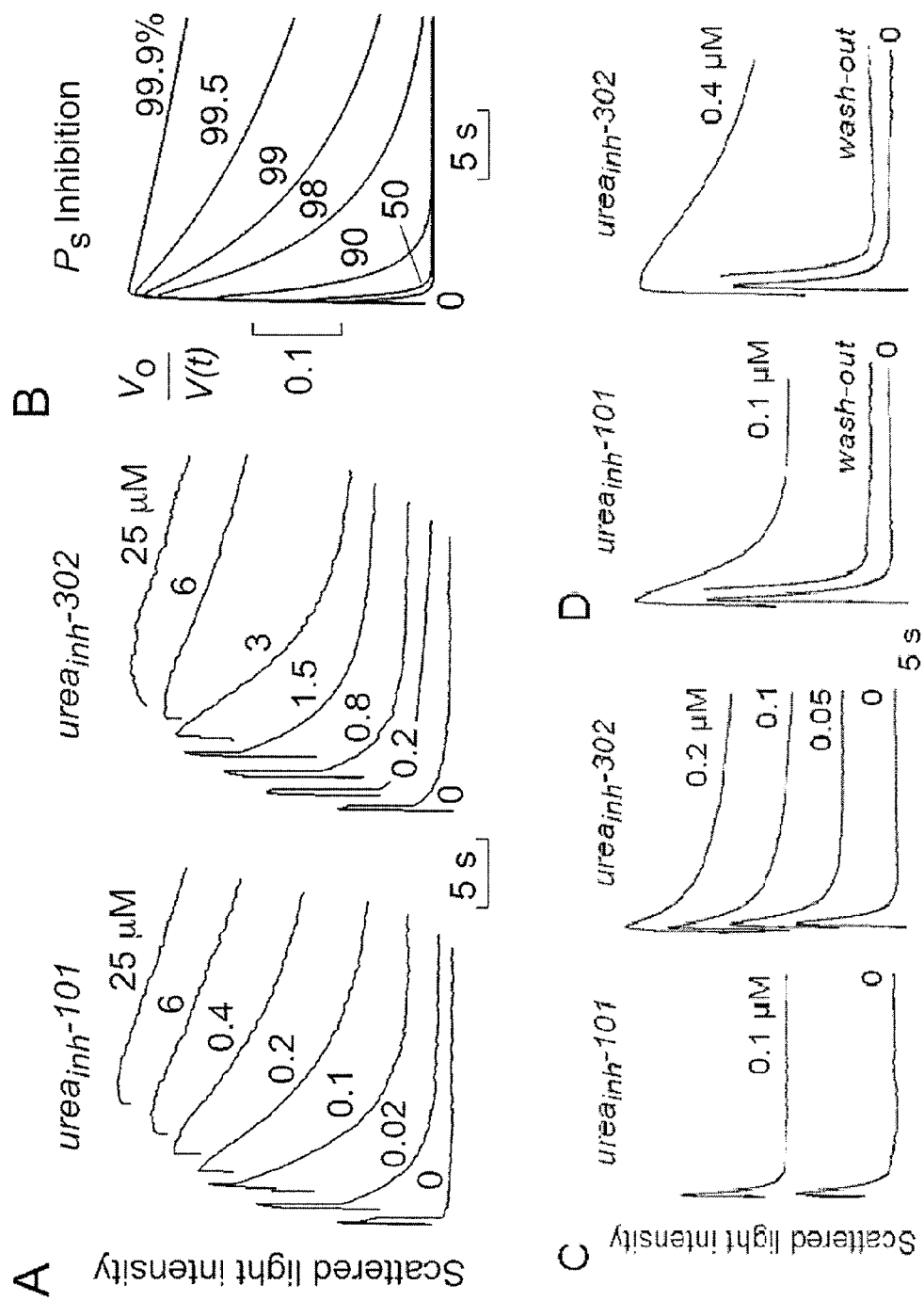
FIGS. 6A-D present stopped-flow measurements of urea transport in human RBCs.

FIG. 6A shows representative data for inhibition of RBC urea transport by the compounds designated $urea_{inh}$-101 and urea$_{inh}$-302. Urea permeability coefficients (P$_s$) were determined from light-scattering curves by numerical integration of the flux equations for coupled RBC water/urea transport as described above. An example of computed concentration-inhibition data is plotted in FIG. 6B. The deduced EC$_{50}$ values from stopped-flow measurements were in general agreement with the EC$_{50}$ values determined in the lysis assay. The computations indicated that 50% UT-B inhibition produces a subtle change (approximately 2-fold slowing) in the light-scattering curve, whereas the more obvious visual evidence for slowed kinetics is seen at >95% inhibition. These computations indicated that many of the inhibitors produced greater than 99% UT-B inhibition.

To determine the sidedness of inhibitor action, compounds were added only to the urea-containing solution (at concentrations 2 times higher than their EC$_{50}$) before mixing with RBCs in stopped-flow measurements. To assay for reversibility, compounds (at concentrations 4 times higher than their EC$_{50}$) were added to RBCs for 10 min and then washed by centrifugation prior to stopped-flow measurements.

RBCs were exposed externally to urea$_{inh}$-101 and urea$_{inh}$-302 at final concentrations of 0.1 and 0.2 µM, respectively (approximately 2 times their EC$_{50}$) just at the time of stopped-flow experiments (inhibitor inclusion only in urea-containing solution). Whereas urea$_{inh}$-101 did not inhibit urea transport under these conditions, suggesting an intracellular site of action, urea$_{inh}$-302 had a sizable effect (see FIG. 6C). The inhibition of urea permeability by externally added urea$_{inh}$-302 was concentration-dependent.

To test reversibility of inhibition, RBCs were pre-incubated with urea$_{inh}$-101 or urea$_{inh}$-302 for 10 min (at 0.1 and 0.4 µM, respectively), which resulted in greater than 95% transport inhibition. After the RBCs were washed, urea transport was identical to transport in RBCs that were not exposed to an inhibitor, indicating fully reversible inhibition (see FIG. 6D).

Example 6

Structure-Activity Analysis (SAR) of Four Classes of UT-B Inhibitors

UT-B inhibitory potencies for the most active compounds of each of the chemical classes are summarized in Tables 1-4.
Class 1 Compounds: Phenylsulfoxyoxazoles and Phenylsulfoxyimidazoles Class 1 compounds included phenylsulfoxyoxazoles, but also included several phenylsulfoxyimidazoles (urea$_{inh}$-130-132) (see Table 1). In highly active compounds, unsubstituted thioglycoamide was present as R1 (urea$_{inh}$-101-119). Compounds with reduced activity often had amino groups such as mono/dialkylated amines (urea$_{inh}$-120-123), n-morpholino (urea$_{inh}$-124-125), and hexahydro-1-H-azepine-1-yl (urea$_{inh}$-126-128) as R1. Compounds were inactive that had R1 as a thioglycoamide or a mono- or dialkylated amide (e.g., —SCH$_2$—CO—NHR or —SCH$_2$—CO—NR$_2$) when R was a phenyl group or bulky aliphatic group. The compounds with the lowest EC$_{50}$ values (EC$_{50}$<100 nM) contained 2-thiophene or phenyl rings at R2. Compounds with 2-furan at R2 also exhibited submicromolar potency. Methyl (Me) or halo substitutions at the 4-position of the phenyl ring of R2 reduced activity, while compounds with 3-, di, or tri-substituted phenyl rings at R2 were inactive. For R3 substitutions, halo and methyl groups conferred substantially greater activity compared to unsubstituted analogs.

TABLE 1

Structure-Activity Analysis of Phenylsulfoxyoxazoles and Phenylsulfoxyimidazoles Class 1:
Phenylsulfoxyoxazoles and
Phenylsulfoxyimidazoles

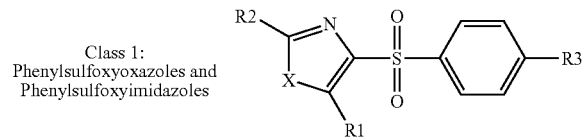

Active compounds

| Compound | X | —R1 | —R2 | —R3 | EC$_{50}$ (µM) |
|---|---|---|---|---|---|
| urea$_{inh}$-101* | O | —S—CH$_2$—CO—NH$_2$ | -Ph | —Br | 0.03 |
| urea$_{inh}$-102* | O | —S—CH$_2$—CO—NH$_2$ | -Ph | —Cl | 0.04 |
| urea$_{inh}$-103* | O | —S—CH$_2$—CO—NH$_2$ | -Ph | -Me | 0.1 |
| urea$_{inh}$-104* | O | —S—CH$_2$—CO—NH$_2$ | -Ph | —H | 1 |
| urea$_{inh}$-105* | O | —S—CH$_2$—CO—NH$_2$ | -(4-F)-Ph | -Me | 0.1 |
| urea$_{inh}$-106 | O | —S—CH$_2$—CO—NH$_2$ | -(4-F)-Ph | —Cl | 0.2 |
| urea$_{inh}$-107* | O | —S—CH$_2$—CO—NH$_2$ | -(4-F)-Ph | —F | 6 |
| urea$_{inh}$-108* | O | —S—CH$_2$—CO—NH$_2$ | -(4-F)-Ph | —H | 15 |
| urea$_{inh}$-109* | O | —S—CH$_2$—CO—NH$_2$ | -(4-Me)-Ph | —Br | 0.2 |
| urea$_{inh}$-110* | O | —S—CH$_2$—CO—NH$_2$ | -(4-Me)-Ph | -Me | 1 |
| urea$_{inh}$-111 | O | —S—CH$_2$—CO—NH$_2$ | -(4-Me)-Ph | —Cl | 1 |
| urea$_{inh}$-112 | O | —S—CH$_2$—CO—NH$_2$ | -(4-Me)-Ph | —H | 15 |
| urea$_{inh}$-113 | O | —S—CH$_2$—CO—NH$_2$ | -2-thiophene | —Cl | 0.02 |
| urea$_{inh}$-114* | O | —S—CH$_2$—CO—NH$_2$ | -2-thiophene | -Me | 0.5 |
| urea$_{inh}$-115 | O | —S—CH$_2$—CO—NH$_2$ | -2-thiophene | —F | 0.6 |
| urea$_{inh}$-116 | O | —S—CH$_2$—CO—NH$_2$ | -2-thiophene | —H | 1 |
| urea$_{inh}$-117* | O | —S—CH$_2$—CO—NH$_2$ | -2-furan | —Cl | 0.1 |
| urea$_{inh}$-118* | O | —S—CH$_2$—CO—NH$_2$ | -2-furan | —Br | 0.2 |
| urea$_{inh}$-119* | O | —S—CH$_2$—CO—NH$_2$ | -2-furan | -Me | 1 |
| urea$_{inh}$-120 | O | —NH—CH$_2$-Ph | -(2-F)-Ph | —Cl | 1 |
| urea$_{inh}$-121 | O | —S—CH$_2$—CO—NH—CH$_2$-2-furan | -Ph | —Br | 4 |
| urea$_{inh}$-122 | O | —S—CH$_2$—CO—NH—CH$_2$-2-furan | -Ph | —Cl | 15 |
| urea$_{inh}$-123 | O | —N(CH$_3$)$_2$ | -(2-Cl)-Ph | —H | 5 |
| urea$_{inh}$-124 | O | -n-morpholino | -(2-F)-Ph | —H | 7 |

TABLE 1-continued

Structure-Activity Analysis of Phenylsulfoxyoxazoles and Phenylsulfoxyimidazoles

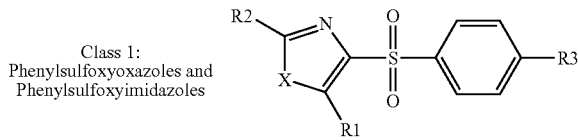

Class 1:
Phenylsulfoxyoxazoles and
Phenylsulfoxyimidazoles

Active compounds

| Compound | X | —R1 | —R2 | —R3 | $EC_{50}$ (µM) |
|---|---|---|---|---|---|
| urea$_{inh}$-125 | O | -n-morpholino | -(2-Cl)-Ph | -Me | 11 |
| urea$_{inh}$-126 | O | -hexahydro-1-H-azepine-1-yl | -(2-OMe)-Ph | —H | 10 |
| urea$_{inh}$-127 | O | -hexahydro-1-H-azepine-1-yl | -(4-Me)-Ph | —H | 10 |
| urea$_{inh}$-128 | O | -hexahydro-1-H-azepine-1-yl | -(4-F)-Ph | —H | 10 |
| urea$_{inh}$-129* | O | —SMe | -2-furan | —Cl | 20 |
| urea$_{inh}$-130* | N | —SMe | -(4-Me)-Ph | —H | 2 |
| urea$_{inh}$-131 | N | —SH | -Ph | -Me | 6 |
| urea$_{inh}$-132 | N | —S—CO-Ph | -Ph | —H | 7 |

Inactive Compounds
R1: SCH$_2$—CO—NR$_2$, SCH$_2$—CO—NHR (R is substituted phenyl (Ph) or bulky aliphatic)
R2: 3-, di-, or tri-substituted phenyls
*Denotes inhibitors identified in primary screening The compound designations and the corresponding compound names for the above Class 1 compounds are provided in Table 2.

TABLE 2

Phenylsulfoxyoxazoles and Phenylsulfoxyimidazoles

| Compound # | Name |
|---|---|
| Urea$_{inh}$-101 | 2-(4-(4-bromophenylsulfonyl)-2-phenyloxazol-5-ylthio)acetamide |
| Urea$_{inh}$-102 | 2-(4-(4-chlorophenylsulfonyl)-2-phenyloxazol-5-ylthio)acetamide |
| Urea$_{inh}$-103 | 2-(2-phenyl-4-tosyloxazol-5-ylthio)acetamide |
| Urea$_{inh}$-104 | 2-(2-phenyl-4-(phenylsulfonyl)oxazol-5-ylthio)acetamide |
| Urea$_{inh}$-105 | 2-(2-(4-fluorophenyl)-4-tosyloxazol-5-ylthio)acetamide |
| Urea$_{inh}$-106 | 2-(4-(4-chlorophenylsulfonyl)-2-(4-fluorophenyl)oxazol-5-ylthio)acetamide |
| Urea$_{inh}$-107 | 2-(2-(4-fluorophenyl)-4-(4-fluorophenylsulfonyl)oxazol-5-ylthio)acetamide |
| Urea$_{inh}$-108 | 2-(2-(4-fluorophenyl)-4-(phenylsulfonyl)oxazol-5-ylthio)acetamide |
| Urea$_{inh}$-109 | 2-(4-(4-bromophenylsulfonyl)-2-p-tolyloxazol-5-ylthio)acetamide |
| Urea$_{inh}$-110 | 2-(2-p-tolyl-4-tosyloxazol-5-ylthio)acetamide |
| Urea$_{inh}$-111 | 2-(4-(4-chlorophenylsulfonyl)-2-p-tolyloxazol-5-ylthio)acetamide |
| Urea$_{inh}$-112 | 2-(4-(phenylsulfonyl)-2-p-tolyloxazol-5-ylthio)acetamide |
| Urea$_{inh}$-113 | 2-(4-(4-chlorophenylsulfonyl)-2-(thiophen-2-yl)oxazol-5-ylthio)acetamide |
| Urea$_{inh}$-114 | 2-(2-(thiophen-2-yl)-4-tosyloxazol-5-ylthio)acetamide |
| Urea$_{inh}$-115 | 2-(4-(4-fluorophenylsulfonyl)-2-(thiophen-2-yl)oxazol-5-ylthio)acetamide |
| Urea$_{inh}$-116 | 2-(4-(phenylsulfonyl)-2-(thiophen-2-yl)oxazol-5-ylthio)acetamide |
| Urea$_{inh}$-117 | 2-(4-(4-chlorophenylsulfonyl)-2-(furan-2-yl)oxazol-5-ylthio)acetamide |
| Urea$_{inh}$-118 | 2-(4-(4-bromophenylsulfonyl)-2-(furan-2-yl)oxazol-5-ylthio)acetamide |
| Urea$_{inh}$-119 | 2-(2-(furan-2-yl)-4-tosyloxazol-5-ylthio)acetamide |
| Urea$_{inh}$-120 | N-benzyl-4-(4-chlorophenylsulfonyl)-2-(2-fluorophenyl)oxazol-5-amine |
| Urea$_{inh}$-121 | 2-(4-(4-bromophenylsulfonyl)-2-phenyloxazol-5-ylthio)-N-(furan-2-ylmethyl)acetamide |
| Urea$_{inh}$-122 | 2-(4-(4-chlorophenylsulfonyl)-2-phenyloxazol-5-ylthio)-N-(furan-2-ylmethyl)acetamide |
| Urea$_{inh}$-123 | 2-(2-chlorophenyl)-N,N-dimethyl-4-(phenylsulfonyl)oxazol-5-amine |
| Urea$_{inh}$-124 | 4-(2-(2-fluorophenyl)-4-(phenylsulfonyl)oxazol-5-yl)morpholine |
| Urea$_{inh}$-125 | 4-(2-(2-chlorophenyl)-4-tosyloxazol-5-yl)morpholine |
| Urea$_{inh}$-126 | 5-(azepan-1-yl)-2-(2-methoxyphenyl)-4-(phenylsulfonyl)oxazole |
| Urea$_{inh}$-127 | 5-(azepan-1-yl)-4-(phenylsulfonyl)-2-p-tolyloxazole |
| Urea$_{inh}$-128 | 5-(azepan-1-yl)-2-(4-fluorophenyl)-4-(phenylsulfonyl)oxazole |
| Urea$_{inh}$-129 | 4-(4-chlorophenylsulfonyl)-2-(furan-2-yl)-5-(methylthio)oxazole |
| Urea$_{inh}$-130 | 5-(methylthio)-4-(phenylsulfonyl)-2-p-tolyl-1H-imidazole |
| Urea$_{inh}$-131 | 2-phenyl-4-tosyl-1H-imidazole-5-thiol |
| Urea$_{inh}$-132 | S-2-phenyl-4-(phenylsulfonyl)-1H-imidazol-5-yl benzothioate |

Class 2: Compounds—Benzenesulfonanilides

Most active benzenesulfonanilides of Class 2 (see Table 3) contained either 2,5-dimethoxy groups (urea$_{inh}$-201-205) or a fused 1,4-dioxane ring at the 3,4 positions (urea$_{inh}$-207-216) of the aniline phenyl, with the former producing greater UT-B inhibition. Compounds with other mono- or di-substitutions at R1/R2, including 3-methoxy, 4-amino, and 3,4-dimethoxy, were inactive. The benzenesulfonamide phenyl ring tolerated a range of mono-substitutions as R3, including bromo, fluoro, thiomethyl, methoxy (OMe), and acetyl (urea$_{inh}$-203-205, 209, 210). However, methoxy and methyl (Me) groups were tolerated as di-substitutions as R3/R5 (urea$_{inh}$-201, 208) and to a lesser extent as R3/R4 (urea$_{inh}$-212, 214).

TABLE 3

Structure-Activity Analysis of Benzenesulfonanilide Compounds

Class 2: Benzenesulfonanilides

Active compounds

| Compound | —R1 | —R2 | —R3 | —R4 | —R5 | $EC_{50}$ (µM) |
|---|---|---|---|---|---|---|
| urea$_{inh}$-201* | 2-OMe | 5-OMe | OMe | H | OMe | 0.3 |
| urea$_{inh}$-202* | 2-OMe | 5-OMe | H | Br | H | 0.4 |
| urea$_{inh}$-203* | 2-OMe | 5-OMe | Br | H | H | 0.7 |
| urea$_{inh}$-204* | 2-OMe | 5-OMe | F | H | H | 1 |
| urea$_{inh}$-205* | 2-OMe | 5-OMe | SMe | H | H | 1 |
| urea$_{inh}$-206* | 4-OMe | —H | i-Pr | OH | $SO_2$-[4-(OMe)-Ph] | 1 |
| urea$_{inh}$-207 | 3-O—$C_2H_4$—O-4 | | H | CO—$NH_2$ | H | 2 |
| urea$_{inh}$-208 | 3-O—$C_2H_4$—O-4 | | Me | H | Me | 4 |
| urea$_{inh}$-209 | 3-O—$C_2H_4$—O-4 | | OMe | H | H | 6 |
| urea$_{inh}$-210 | 3-O—$C_2H_4$—O-4 | | CO-Me | H | H | 6 |
| urea$_{inh}$-211 | 3-O—$C_2H_4$—O-4 | | Br | H | H | 8 |
| urea$_{inh}$-212 | 3-O—$C_2H_4$—O-4 | | H | Me | H | 10 |
| urea$_{inh}$-213 | 3-O—$C_2H_4$—O-4 | | | 3-$C_4H_4$-4 | H | 10 |
| urea$_{inh}$-214 | 3-O—$C_2H_4$—O-4 | | OMe | OMe | H | 15 |
| urea$_{inh}$-215 | 3-O—$C_2H_4$—O-4 | | $CF_3$ | H | H | 15 |
| urea$_{inh}$-216 | 3-O—$C_2H_4$—O-4 | | H | NH—CO-Me | H | 15 |
| urea$_{inh}$-217 | 3-O—CO—N(Me)-4 | | $CF_3$ | H | H | 4 |

Inactive Compounds
R1, R2: 3,4-di-OMe, 3-OMe, 4-amino
R3, R5: di-(halo/carboxy)
R4: acetyl, Ph-acetyl, Me, OMe, F, sulfonyl-amino
*Denotes inhibitors identified in primary screening The compound designations and the corresponding compound names for the above Class 2 compounds are provided in Table 4.

TABLE 4

Benzenesulfonanilide Compounds

| Compound # | Name |
|---|---|
| Urea$_{inh}$-201 | N-(2,5-dimethoxyphenyl)-3,5-dimethoxybenzenesulfonamide |
| Urea$_{inh}$-202 | 4-bromo-N-(2,5-dimethoxyphenyl) benzenesulfonamide |
| Urea$_{inh}$-203 | 3-bromo-N-(2,5-dimethoxyphenyl) benzenesulfonamide |
| Urea$_{inh}$-204 | N-(2,5-dimethoxyphenyl)-3-fluorobenzenesulfonamide |
| Urea$_{inh}$-205 | N-(2,5-dimethoxyphenyl)-3-(methylthio) benzenesulfonamide |
| Urea$_{inh}$-206 | 4-hydroxy-3-isopropyl-N-(4-methoxyphenyl)-5-(4-methoxyphenylsulfonyl) benzenesulfonamide |
| Urea$_{inh}$-207 | 4-(N-(2,3-dihydrobenzo [b][1,4]dioxin-6-yl) sulfamoyl)benzamide |
| Urea$_{inh}$-208 | N-(2,3-dihydrobenzo [b][1,4]dioxin-6-yl)-3,5-dimethylbenzenesulfonamide |
| Urea$_{inh}$-209 | N-(2,3-dihydrobenzo [b][1,4]dioxin-6-yl)-3-methoxybenzenesulfonamide |
| Urea$_{inh}$-210 | 3-acetyl-N-(2,3-dihydrobenzo [b][1,4]dioxin-6-yl) benzenesulfonamide |
| Urea$_{inh}$-211 | 3-bromo-N-(2,3-dihydrobenzo[b][1,4]dioxin-6-yl)benzenesulfonamide |
| Urea$_{inh}$-212 | N-(2,3-dihydrobenzo[b][1,4] dioxin-6-yl)-3,4-dimethylbenzenesulfonamide |
| Urea$_{inh}$-213 | N-(2,3-dihydrobenzo[b][1,4] dioxin-6-yl)naphthalene-2-sulfonamide |
| Urea$_{inh}$-214 | N-(2,3-dihydrobenzo[b][1,4] dioxin-6-yl)-3,4-dimethoxybenzenesulfonamide |

TABLE 4-continued

Benzenesulfonanilide Compounds

| Compound # | Name |
|---|---|
| Urea$_{inh}$-215 | N-(2,3-dihydrobenzo [b][1,4]dioxin-6-yl)-3(trifluoromethyl) benzenesulfonamide |
| Urea$_{inh}$-216 | N-(4-(N-(2,3-dihydrobenzo [b][1,4]dioxin-6-yl)sulfamoyl) phenyl)acetamide |
| Urea$_{inh}$-217 | N-(3-methyl-2-oxo-2,3-dihydrobenzo[d]oxazol-6-yl)-3-(trifluoromethyl) benzenesulfonamide |

Class 3 Compounds—Phthalazinamines

SAR of Class 3 phthalazinamines (see Table 5) indicated preferred mono-substitution at the 4 position of the 4-phenyl ring, especially with carboxamide or methoxy functions (urea$_{inh}$-301-308, 312, 313). Other acceptable 4-phenyl mono-substitutions included 4-methyl, 4-hydroxy, 4-diethylcarboxamide, and 4-n-hydroethylcarboxamide (urea$_{inh}$-309-311, 314-317). Active phthalazinamines that contained di-substitutions on this phenyl ring combined methyl (Me) at the 3-position with a variety of unsubstituted and mono/di-alkylated sulfanoyls at the 4-position (urea$_{inh}$-321-331). Alkylation of 1-amino resulted in complete loss of activity, whereas replacement by oxygen reduced activity partially (urea$_{inh}$-332, 333). Inhibitory activity was also lost when the 1-amino group was substituted by phenylmethyl rather than phenyl. Analogs were active when the n-phenyl-1-amino moiety was substituted at the 4-position, particularly with methyl and methoxy groups and mono/di-alkylated carboxamides (urea$_{inh}$-301-304); also well tolerated as R3 were hydroxy, sulfanoyl, glycoamide, and n-methyl-glycoamide substitutions (urea$_{inh}$-306, 307, 311, 312).

TABLE 5

Structure-activity analysis of phthalazinamines.

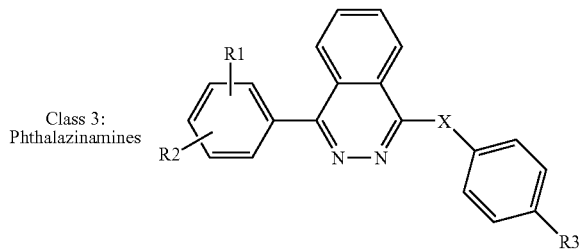

Class 3: Phthalazinamines

Active compounds

| Compound | X | —R1 | —R2 | —R3 | EC$_{50}$ (μM) |
|---|---|---|---|---|---|
| urea$_{inh}$-301 | NH | 4-CO—NH$_2$ | —H | OMe | 0.1 |
| urea$_{inh}$-302 | NH | 4-CO—NH$_2$ | —H | Me | 0.2 |
| urea$_{inh}$-303 | NH | 4-CO—NH$_2$ | —H | CO—N(Me)$_2$ | 0.2 |
| urea$_{inh}$-304 | NH | 4-CO—NH$_2$ | —H | CO—NH-Me | 0.6 |
| urea$_{inh}$-305 | NH | 4-CO—NH$_2$ | —H | pyran | 0.7 |
| urea$_{inh}$-306 | NH | 4-CO—NH$_2$ | —H | OH | 2 |
| urea$_{inh}$-307 | NH | 4-CO—NH$_2$ | —H | SO$_2$—NH$_2$ | 3 |
| urea$_{inh}$-308 | NH | 4-CO—N(Et)$_2$ | —H | CO—NH-Me | 2 |
| urea$_{inh}$-309 | NH | 4-CO—N(Et)$_2$ | —H | OH | 5 |
| urea$_{inh}$-310 | NH | 4-CO—N(Et)$_2$ | —H | CO—N(Me)$_2$ | 3 |
| urea$_{inh}$-311 | NH | 4-CO—NH—C$_2$H$_4$—OH | —H | O—CH$_2$—CO—NH-Me | 0.8 |
| urea$_{inh}$-312 | NH | 4-OMe | —H | O—CH$_2$—CO—NH$_2$ | 1 |
| urea$_{inh}$-313 | NH | 4-OMe | —H | 2-benzimidazole | 10 |
| urea$_{inh}$-314 | NH | 4-Me | —H | O—CH$_2$—CO—NH$_2$ | 2 |
| urea$_{inh}$-315 | NH | 4-Me | —H | O—CH$_2$—CO—NH-Me | 2 |
| urea$_{inh}$-316* | NH | 4-OH | —H | OMe | 2 |
| urea$_{inh}$-317* | NH | 4-OH | —H | NH—CO-Me | 3 |
| urea$_{inh}$-318 | NH | —H | —H | O—CH$_2$—CO—NH$_2$ | 2 |
| urea$_{inh}$-319 | NH | —H | —H | O—CH$_2$—CO—NH-Me | 3 |
| urea$_{inh}$-320 | NH | —H | —H | OMe | 4 |
| urea$_{inh}$-321 | NH | 3-SO$_2$—N(Me)$_2$ | 4-Me | CO—NH$_2$ | 1 |
| urea$_{inh}$-322 | NH | 3-SO$_2$—N(Me)$_2$ | 4-Me | O—CH$_2$—CO—NH$_2$ | 2 |
| urea$_{inh}$-323 | NH | 3-SO$_2$—NH—C$_2$H$_2$—OH | 4-Me | CO—OMe | 2 |
| urea$_{inh}$-324 | NH | 3-SO$_2$—NH—C$_2$H$_2$—OH | 4-Me | CO—NH$_2$ | 5 |
| urea$_{inh}$-325 | NH | 3-SO$_2$—NH-Me | 4-Me | O—CH$_2$—CO—NH$_2$ | 2 |
| urea$_{inh}$-326 | NH | 3-SO$_2$—NH-Me | 4-Me | O—CH$_2$—CO—NH-Me | 2 |
| urea$_{inh}$-327 | NH | 3-SO$_2$—NH-Me | 4-Me | CO—NH-Me | 2 |
| urea$_{inh}$-328 | NH | 3-SO$_2$-n-morpholino | 4-Me | OH | 3 |
| urea$_{inh}$-329 | NH | 3-SO$_2$—NH$_2$ | 4-Me | CO—NH$_2$ | 5 |
| urea$_{inh}$-330 | NH | 3-SO$_2$—NH$_2$ | 4-Me | O—CH$_2$—CO—NH-Me | 10 |
| urea$_{inh}$-331 | NH | 3-SO$_2$—NH—C(Me)$_2$(CH$_2$—OH) | 4-Me | OH | 9 |
| urea$_{inh}$-332 | O | 4-OMe | —H | H | 2 |
| urea$_{inh}$-333 | O | 4-Me | —H | H | 3 |

Inactive Compounds
X: NR, when R is any aliphatic
*Denotes inhibitors identified in primary screening The compound designations and the corresponding compound names for the above Class 3 compounds are provided in Table 6.

TABLE 6

Phthalazinamine Compounds

| Compound # | Name |
|---|---|
| Urea$_{inh}$-301 | 4-(4-(4-methoxyphenylamino) phthalazin-1-yl)benzamide |
| Urea$_{inh}$-302 | 4-(4-(p-tolylamino)phthalazin-1-yl)benzamide |
| Urea$_{inh}$-303 | 4-(4-(4-carbamoylphenyl) phthalazin-1-ylamino)-N,N-dimethylbenzamide |
| Urea$_{inh}$-304 | 4-(4-(4-carbamoylphenyl) phthalazin-1-ylamino)-N-methylbenzamide |
| Urea$_{inh}$-305 | 4-(4-(4-(2H-pyran-2-yl)phenylamino)phthalazin-1-yl)benzamide |
| Urea$_{inh}$-306 | 4-(4-(4-hydroxyphenylamino) phthalazin-1-yl)benzamide |
| Urea$_{inh}$-307 | 4-(4-(4-sulfamoylphenylamino) phthalazin-1-yl)benzamide |
| Urea$_{inh}$-308 | N,N-diethyl-4-(4-(4-(methylcarbamoyl)phenylamino)phthalazin-1-yl)benzamide |
| Urea$_{inh}$-309 | N,N-diethyl-4-(4-(4-hydroxyphenylamino) phthalazin-1-yl)benzamide |
| Urea$_{inh}$-310 | 4-(4-(4-(diethylcarbamoyl) phenyl)phthalazin-1-ylamino)-N,N-dimethylbenzamide |
| Urea$_{inh}$-311 | N-(2-hydroxyethyl)-4-(4-(4-(2-(methylamino)-2-oxoethoxy)phenylamino) phthalazin-1-yl)benzamide |
| Urea$_{inh}$-312 | 2-(4-(4-(4-methoxyphenyl) phthalazin-1-ylamino) phenoxy)acetamide |
| Urea$_{inh}$-313 | N-(4-(1H-benzo[d]imidazol-2-yl)phenyl)-4-(4-methoxyphenyl) phthalazin-1-amine |

TABLE 6-continued

Phthalazinamine Compounds

| Compound # | Name |
|---|---|
| Urea$_{inh}$-314 | 2-(4-(4-p-tolylphthalazin-1-ylamino)phenoxy) acetamide |
| Urea$_{inh}$-315 | N-methyl-2-(4-(4-p-tolylphthalazin-1-ylamino) phenoxy)acetamide |
| Urea$_{inh}$-316 | 4-(4-(4-methoxyphenylamino) phthalazin-1-yl)phenol |
| Urea$_{inh}$-317 | N-(4-(4-(4-hydroxyphenyl) phthalazin-1-ylamino) phenyl)acetamide |
| Urea$_{inh}$-318 | 2-(4-(4-phenylphthalazin-1-ylamino)phenoxy) acetamide |
| Urea$_{inh}$-319 | N-methyl-2-(4-(4-phenylphthalazin-1-ylamino) phenoxy)acetamide |
| Urea$_{inh}$-320 | N-(4-methoxyphenyl)-4-phenylphthalazin-1-amine |
| Urea$_{inh}$-321 | 4-(4-(3-(N,N-dimethylsulfamoyl)-4-methylphenyl) phthalazin-1-ylamino) benzamide |
| Urea$_{inh}$-322 | 2-(4-(4-(3-(N,N-dimethylsulfamoyl)-4-methylphenyl) phthalazin-1-ylamino) phenoxy)acetamide |
| Urea$_{inh}$-323 | methyl 4-(4-(3-(N-(2-hydroxyethyl)sulfamoyl)-4-methylphenyl) phthalazin-1-ylamino) benzoate |
| Urea$_{inh}$-324 | 4-(4-(3-(N-(2-hydroxyethyl)sulfamoyl)-4-methylphenyl) phthalazin-1-ylamino) benzamide |
| Urea$_{inh}$-325 | 2-(4-(4-(4-methyl-3-(N-methylsulfamoyl)phenyl) phthalazin-1-ylamino) phenoxy)acetamide |
| Urea$_{inh}$-326 | N-methyl-2-(4-(4-(4-methyl-3-(N-methylsulfamoyl) phenyl)phthalazin-1-ylamino)phenoxy) acetamide |
| Urea$_{inh}$-327 | 4-(4-(4-methyl-3-(N-methylsulfamoyl)phenyl)phthalazin-1-ylamino)benzamide |
| Urea$_{inh}$-328 | 4-(4-(4-methyl-3-(morpholinosulfonyl) phenyl)phthalazin-1-ylamino)phenol |
| Urea$_{inh}$-329 | 4-(4-(4-methyl-3-sulfamoylphenyl) phthalazin-1-ylamino) benzamide |
| Urea$_{inh}$-330 | N-methyl-2-(4-(4-(4-methyl-3-sulfamoylphenyl) phthalazin-1-ylamino) phenoxy)acetamide |
| Urea$_{inh}$-331 | N-(1-hydroxy-2-methylpropan-2-yl)-5-(4-(4-hydroxyphenylamino)phthalazin-1-yl)-2-methylbenzenesulfonamide |
| Urea$_{inh}$-332 | 1-(4-methoxyphenyl)-4-phenoxyphthalazine |
| Urea$_{inh}$-333 | 1-phenoxy-4-p-tolylphthalazine |

Class 4 Compounds—Aminobenzimidazoles

For the Class 4 aminobenzimidazoles (see Table 7), no substitutions were allowed at R1 except for methyl, which reduced activity (urea$_{inh}$-404 vs. 423). The 2-hydroxyphenyl-methyl group was present in active compounds; inhibitory activity was eliminated by replacement of hydroxy with methoxy or substituted sulfonyl amino groups. Without wishing to be bound by theory, the loss of activity upon hydroxymethylation could be due to disruption of hydrogen bond donor effects. Additional substitutions at the benzyl function, such as 5-bromo, 5-chloro, and 5-methyl, increased activity (urea$_{inh}$-401-406, 414-417), though compounds without 5-position substitutions were also active (urea$_{inh}$-407-413). By contrast, compounds with substituents at the 3-, 4- or 6-positions were generally inactive. Alkylation of the imidazole nitrogen (R3) was favorable, especially with ethyl (Et), n-propyl (n-Pr), isopropyl (i-Pr), and 2-propenyl groups (urea$_{inh}$-401-406, 409-411, 414-416). Several bulky alkyl chains comprising substituted amino functions were also active (urea$_{inh}$-407, 408).

TABLE 7

Structure-Activity Analysis of Aminobenzimidazole Compounds

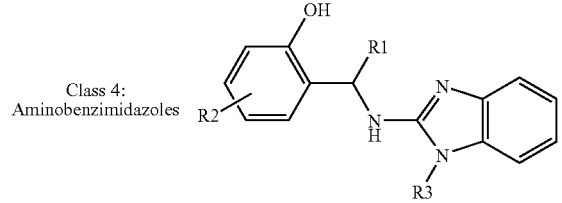

Class 4: Aminobenzimidazoles

Active compounds

| Compound | —R1 | —R2 | —R3 | EC$_{50}$ (µM) |
|---|---|---|---|---|
| urea$_{inh}$-401 | H | 5-Cl | -n-Pr | 0.3 |
| urea$_{inh}$-402 | H | 5-Cl | -Et | 0.4 |
| urea$_{inh}$-403* | H | 5-Cl | -i-Pr | 5 |
| urea$_{inh}$-404 | H | 5-Br | Et | 0.4 |
| urea$_{inh}$-405* | H | 5-Br | -i-Pr | 0.4 |
| urea$_{inh}$-406* | H | 5-Br | —CH$_2$—CH=CH$_2$ | 1 |
| urea$_{inh}$-407 | H | —H | —C$_2$H$_2$—N(Et)$_2$ | 0.8 |
| urea$_{inh}$-408 | H | —H | —C$_2$H$_4$-n-piperidine | 0.9 |
| urea$_{inh}$-409 | H | —H | -Et | 2 |
| urea$_{inh}$-410 | H | —H | -n-Pr | 2 |
| urea$_{inh}$-411 | H | —H | -i-Pr | 5 |
| urea$_{inh}$-412 | H | —H | —C$_2$H$_4$-n-morpholino | 6 |
| urea$_{inh}$-413 | H | —H | —CH$_2$—CH=CH$_2$ | 9 |
| urea$_{inh}$-414 | H | 5-Me | -n-Pr | 1 |
| urea$_{inh}$-415 | H | 5-Me | -i-Pr | 1 |
| urea$_{inh}$-416 | H | 5-Me | -Et | 1 |
| urea$_{inh}$-417 | H | 5-Me | -n-Bu | 2 |
| urea$_{inh}$-418 | H | 5-OMe | -n-Pr | 6 |
| urea$_{inh}$-419 | H | 5-OMe | —CH$_2$—CH=CH$_2$ | 25 |
| urea$_{inh}$-420 | H | 5-OMe | -i-Pr | 3 |
| urea$_{inh}$-421 | H | 5-C$_4$H$_4$-6 | -Et | 3 |
| urea$_{inh}$-422 | H | 3-OMe | -Et | 11 |
| urea$_{inh}$-423 | Me | 5-Cl | -Et | 5 |

Inactive Compounds
R1: Me reduces activity, bulkier aliphatics are inactive
R2: most 3-, 4-, 6-substitutions
*Denotes inhibitors identified in primary screening The compound designations and the corresponding compound names for the above Class 4 compounds are provided in Table 8.

TABLE 8

Aminobenzimidazole Compounds

| Compound # | Name |
|---|---|
| Urea$_{inh}$-401 | 4-chloro-2-((1-propyl-1H-benzo[d]imidazol-2-ylamino)methyl)phenol |
| Urea$_{inh}$-402 | 4-chloro-2-((1-ethyl-1H-benzo[d]imidazol-2-ylamino)methyl)phenol |
| Urea$_{inh}$-403 | 4-chloro-2-((1-isopropyl-1H-benzo[d]imidazol-2-ylamino)methyl)phenol |
| Urea$_{inh}$-404 | 4-bromo-2-((1-ethyl-1H-benzo[d]imidazol-2-ylamino)methyl)phenol |
| Urea$_{inh}$-405 | 4-bromo-2-((1-isopropyl-1H-benzo[d]imidazol-2-ylamino)methyl)phenol |
| Urea$_{inh}$-406 | 2-((1-allyl-1H-benzo[d]imidazol-2-ylamino)methyl)-4-bromophenol |
| Urea$_{inh}$-407 | 2-((1-(2-(diethylamino)ethyl)-1H-benzo[d]imidazol-2-ylamino)methyl)phenol |
| Urea$_{inh}$-408 | 2-((1-(2-(piperidin-1-yl)ethyl)-1H-benzo[d]imidazol-2-ylamino)methyl)phenol |
| Urea$_{inh}$-409 | 2-((1-ethyl-1H-benzo[d]imidazol-2-ylamino)methyl)phenol |
| Urea$_{inh}$-410 | 2-((1-propyl-1H-benzo[d]imidazol-2-ylamino)methyl)phenol |
| Urea$_{inh}$-411 | 2-((1-isopropyl-1H-benzo[d]imidazol-2-ylamino)methyl)phenol |

TABLE 8-continued

Aminobenzimidazole Compounds

| Compound # | Name |
|---|---|
| Urea$_{inh}$-412 | 2-((1-(2-morpholinoethyl)-1H-benzo[d]imidazol-2-ylamino)methyl)phenol |
| Urea$_{inh}$-413 | 2-((1-allyl-1H-benzo[d]imidazol-2-ylamino)methyl)phenol |
| Urea$_{inh}$-414 | 4-methyl-2-((1-propyl-1H-benzo[d]imidazol-2-ylamino)methyl)phenol |
| Urea$_{inh}$-415 | 2-((1-isopropyl-1H-benzo[d]imidazol-2-ylamino)methyl)-4-methylphenol |
| Urea$_{inh}$-416 | 2-((1-ethyl-1H-benzo[d]imidazol-2-ylamino)methyl)-4-methylphenol |
| Urea$_{inh}$-417 | 2-((1-butyl-1H-benzo[d]imidazol-2-ylamino)methyl)-4-methylphenol |
| Urea$_{inh}$-418 | 4-methoxy-2-((1-propyl-1H-benzo[d]imidazol-2-ylamino)methyl)phenol |
| Urea$_{inh}$-419 | 2-((1-allyl-1H-benzo[d]imidazol-2-ylamino)methyl)-4-methoxyphenol |
| Urea$_{inh}$-420 | 2-((1-isopropyl-1H-benzo[d]imidazol-2-ylamino)methyl)-4-methoxyphenol |
| Urea$_{inh}$-421 | 1-((1-ethyl-1H-benzo[d]imidazol-2-ylamino)methyl)naphthalen-2-ol |
| Urea$_{inh}$-422 | 2-((1-ethyl-1H-benzo[d]imidazol-2-ylamino)methyl)-6-methoxyphenol |
| Urea$_{inh}$-423 | 4-chloro-2-(1-(1-ethyl-1H-benzo[d]imidazol-2-ylamino)ethyl)phenol |

Example 7

Effect of UT-B Inhibitors on Rodent Urea Transport

To identify UT-B inhibitors that would be useful for studies in mouse models, the inhibitors of human UT-B were screened for activity against mouse UT-B in the RBC lysis assay, performed essentially as described in Example 1. Whereas many phenylsulfoxyoxazole compounds and phthalazinamine compounds were highly active against human UT-B were active against mouse UT-B in the RBC lysis assay, none of the benzenesulfonanilide or aminobenzimidazole compounds were active against mouse UT-B in the RBC lysis assay at concentrations as high as 25 µM. The amino acid sequences of human UT-B and murine UT-B exhibit approximately 85% sequence identity (Yang et al., supra). Similar UT-B inhibitory potencies were measured in assays using mouse RBCs and in assays using rat RBCs, which was not unexpected in view of the closely related amino acid sequences of murine and rat UT-B.

Figure 7:
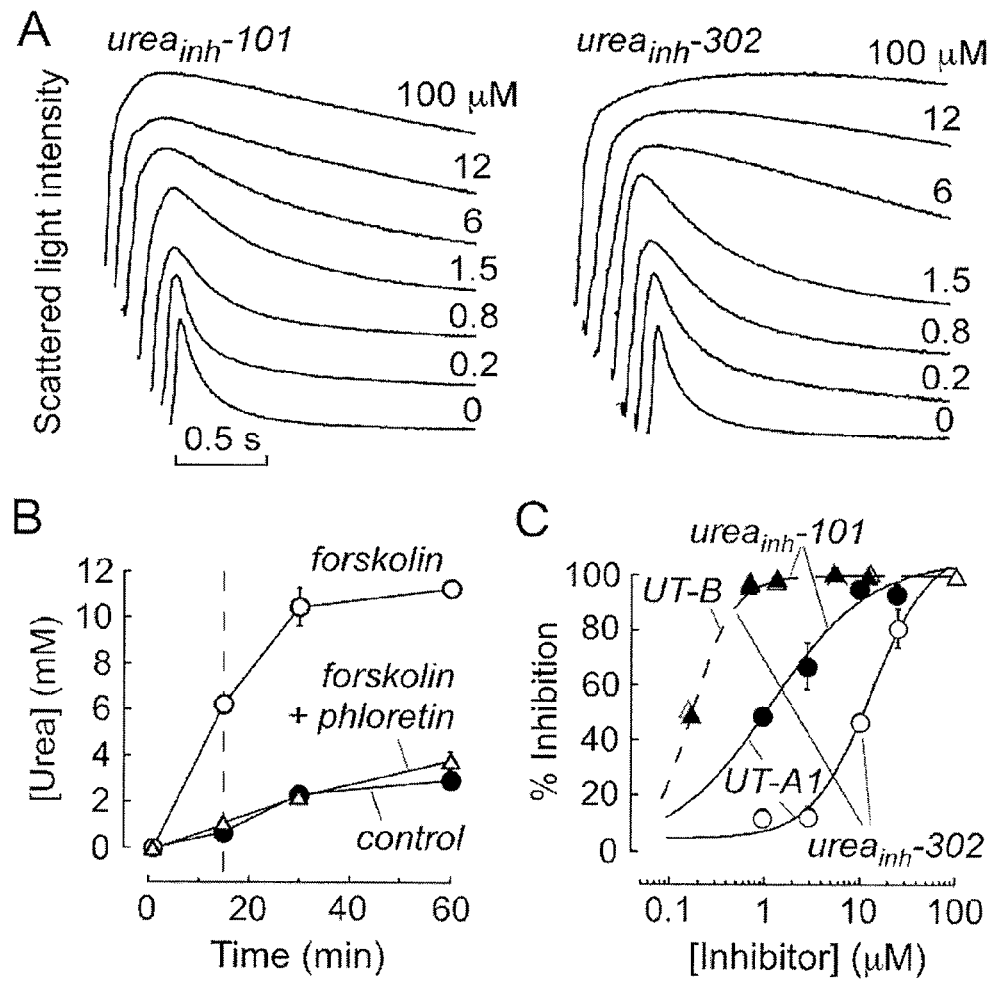
FIGS. 7A-C illustrate activity of UT-B inhibitors against rodent UT-B and UT-A1.

EC$_{50}$ values for the most potent compounds that exhibited activity in the mouse RBC lysis assay were determined by stopped-flow light scattering (see Example 3). Representative curves for two UT-B inhibitors (urea$_{inh}$-101 and urea$_{inh}$-302) are shown in FIG. 7A. For these studies using mouse RBCs, methylurea was used as the transported solute instead of urea because its transport is slower, allowing better estimation of EC$_{50}$ values. Concentration-inhibition data indicated that the most potent phenylsulfoxyoxazole compounds and phthalazinamine compounds had an EC$_{50}$ of approximately 200 nM for mouse UT-B. These compounds, when tested at 25 µM, did not affect urea transport in RBCs from UT-B-null mice.

Example 8

Effect of UT-B Inhibitors on UT-A Transporter

Concentration-inhibition studies were performed to study the effect of the active mouse UT-B inhibitors on urea transport by UT-A. The amino acid sequences of UT-B and UT-A urea transporter isoforms share significant similarity. The cells used in these studies were MDCK cells that expressed rat UT-A1. MDCK-UT-A1-expressing cells were grown on collagen-coated porous filters until they were electrically tight, at which point 15 mM urea was introduced into buffer bathing the basolateral cell surface.

MDCK cells stably transfected with rat UT-A1 (MDCK-UT-A1) (Fröhlich et al., *Am J Physiol*. in press; Fröhlich et al., *Am. J. Physiol. Cell Physiol*. 286:C1264-70 (2004). Epub on Jan. 28, 2004) were generously provided by Dr. Jeffrey Sands (Emory University School of Medicine, Atlanta, Ga.). Cells were grown in Dulbecco's Modified Eagle Medium (DMEM) with bicarbonate and supplemented with 10% fetal bovine serum (FBS), 25 mM HEPES buffer, penicillin G (100 U/mL), streptomycin (100 µg/mL) and hygromycin (500 µg/mL). For determining urea flux, cells were grown on 12-mm collagen-coated TRANSWELL inserts (0.4 µm pore size; Costar) as described (Fröhlich et al., *Am J Physiol*. in press; Fröhlich et al., 2004, supra). The TRANSWELL inserts were incubated in hygromycin-free medium for 1 hr in a 5% CO$_2$ tissue culture incubator (37° C.), and then 2×10$^5$ cells/cm$^2$ were loaded onto each insert. Cells were used after culturing the cells for 4 days in hygromycin-free medium, at which time they formed tight monolayers (transepithelial resistance 500-600 Ω·cm$^2$).

UT-A1-facilitated urea flux in the basolateral-to-apical direction across unstimulated and forskolin-stimulated MDCK-UT-A1 cell layers was measured in response to a 15-mM urea gradient. Experiments were carried out in 12-well plates in which PBS, containing either DMSO vehicle or forskolin, with or without UT-B inhibitor, added to both the apical-facing (0.2 mL) and basal-facing (1 mL) surfaces of cells on the porous filters. Cultures were incubated in the absence of urea for 30 min at 37° C. Then, the basal-facing solution was replaced with PBS (containing same components) with 15 mM urea. Five µL samples of apical fluid were collected at specified times during incubation at 37° C., and urea concentration was determined using a commercial kit based on chromogenic urea complexation at 520-nm wavelength (Quantichrom™ Urea Assay Kit, BioAssay Systems, Hayward, Calif.). Forskolin (10 µM), with or without UT-B transport inhibitors, was added from 1000×DMSO stock solutions (0.2% final DMSO content). Inhibition of UT-A1-mediated transport was defined as % inhibition=100%· $(A_{forsk}-A_{test})/(A_{forsk}-A_{phlor})$. $A_{forsk}$ and $A_{phlor}$ were averaged absorbance values (at 520 nm) for cultures treated with forskolin and forskolin+phloretin, respectively, and $A_{test}$ were values from cultures treated with forskolin+ test compound.

FIG. 7B illustrates the kinetics of urea appearance in the apical solution. UT-A1-facilitated urea transport was strongly increased by the cAMP agonist forskolin and inhibited by phloretin (Fröhlich et al., *Am J Physiol*. in press; Fröhlich et al., 2004, supra). Concentration-inhibition data were obtained at a 15-min time point when urea accumulation in the apical bathing solution is approximately linear. Urea$_{inh}$-101 was more active (EC$_{50}$ equaled approximately 1.2 µM) against rat UT-A1 than urea$_{inh}$-302 (EC$_{50}$ equaled approximately 15 µM) (FIG. 7C). For comparison, concentration-inhibition data are shown for mouse UT-B, which indicates selectivity of these compounds for UT-B over UT-A1. Neither urea$_{inh}$-201 at 25 µM nor urea$_{inh}$-404 at 25 µM significantly inhibited rat UT-A1.

Example 9

Effect of UT-B Inhibitors on UT-B-Facilitated Water Transport

Figure 8:
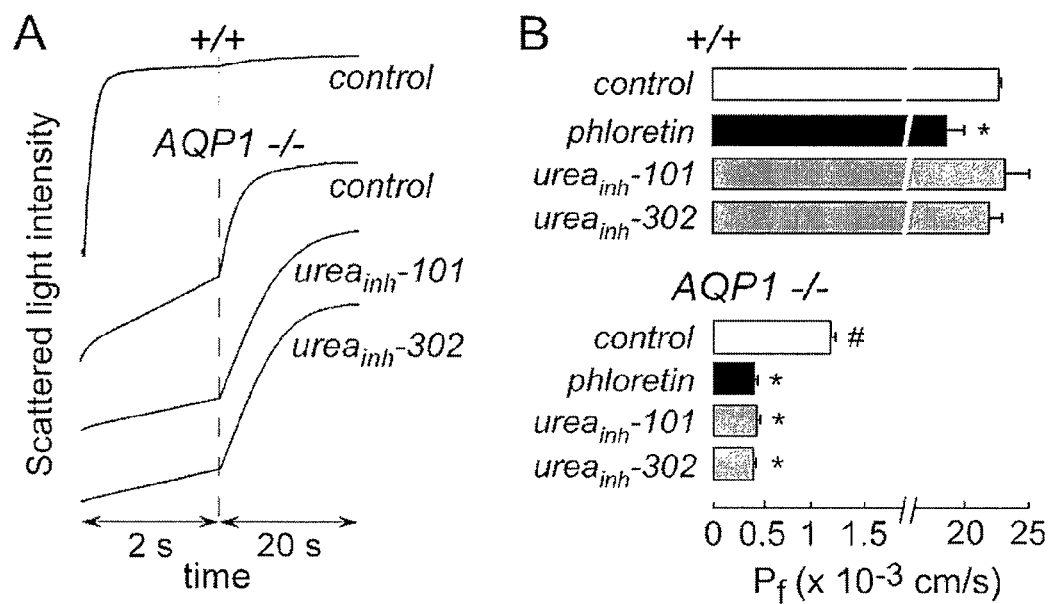
FIGS. 8A-B illustrate UT-B-facilitated water transport by 'chemical UT-B knock-out'. Osmotic water permeability was measured from the time course of RBC volume in response to a 250-mM inwardly directed sucrose gradient.

This example describes chemical knock-out of UT-B by UT-B inhibitors in RBCs and the effect on UT-B-facilitated water transport. Compounds, urea$_{inh}$-101 and urea$_{inh}$-302, which have good inhibitory potencies against mouse UT-B, were used to test the hypothesis that UT-B contains a pore that conducts water in response to an osmotic gradient. Osmotic water permeability was measured by stopped-flow light scattering in RBCs from wild-type and AQP1-null mice as shown in FIG. 8A. Water permeability coefficients are summarized in FIG. 8B. The UT-B inhibitors phloretin, urea$_{inh}$-101, and urea$_{inh}$-302 had little effect on water transport in RBCs from wild-type mice, as expected because AQP1 provides the principal route for water transport. Phloretin at 0.7 mM produced a small but significant reduction in P$_f$ that was likely due to its non-specific effects on membrane fluidity. AQP1-null RBCs had greater than 5-fold reduced P$_f$ compared to wild-type RBCs. As illustrated in FIG. 8B, urea$_{inh}$-101 and urea$_{inh}$-302 further inhibited water permeability in AQP1-null RBCs, indicating that UT-B-facilitated water transport occurs in the cells.

All the above U.S. patents, U.S. patent application publications, U.S. patent applications, foreign patents, foreign patent applications, and non-patent publications referred to in this specification and/or listed in the Application Data Sheet, are incorporated herein by reference, in their entirety.

From the foregoing, although specific embodiments of the invention have been described herein for purposes of illustration, various modifications may be made without deviating from the spirit and scope of the invention. Those skilled in the art will recognize, or be able to ascertain, using no more than routine experimentation, many equivalents to the specific embodiments of the invention described herein. Such equivalents are intended to be encompassed by the following claims.

We claim the following:

1. A method for treating a disease or disorder associated with a urea clearance insufficiency in a subject, said method comprising administering to the subject a composition comprising a pharmaceutically suitable excipient and a compound that inhibits transport of urea by the urea transporter across a cell membrane, wherein the compound is selected from N-benzyl-4-(4-chlorophenylsulfonyl)-2-(2-fluorophenyl)oxazol-5-amine; 5-(methylthio)-4-(phenylsulfonyl)-2-p-tolyl-1H-imidazole; 2-phenyl-4-tosyl-1H-imidazole-5-thiol; and S-2-phenyl-4-(phenylsulfonyl)-1H-imidazol-5-yl benzothioate.

2. The method of claim 1, wherein the disease or disorder is selected from a cardiovascular disease, syndrome of inappropriate antidiuretic hormone secretion (SIADH), cirrhosis, azotemia, acute renal failure, chronic renal insufficiency, fluid retention, diabetes, and abnormal uresis.

3. The method of claim 1 wherein the urea transporter is Urea Transporter-B (UT-B).

* * * * *